(12) United States Patent  
Fleischhauer

(10) Patent No.: US 8,513,120 B2
(45) Date of Patent: Aug. 20, 2013

(54) GOLD-TIN ETCH USING COMBINATION OF HALOGEN PLASMA AND WET ETCH

(75) Inventor: Bruce C Fleischhauer, Chandler, AZ (US)

(73) Assignee: Medtronic, Inc., Minneapolis, MN (US)

( * ) Notice: Subject to any disclaimer, the term of this patent is extended or adjusted under 35 U.S.C. 154(b) by 189 days.

(21) Appl. No.: 13/097,026

(22) Filed: Apr. 28, 2011

(65) Prior Publication Data

US 2011/0269311 A1 Nov. 3, 2011

Related U.S. Application Data

(60) Provisional application No. 61/329,157, filed on Apr. 29, 2010.

(51) Int. Cl.
*H01L 21/306* (2006.01)
*H01L 21/28* (2006.01)

(52) U.S. Cl.
USPC .......... 438/667; 438/754; 257/E21.158; 257/E21.219

(58) Field of Classification Search
None
See application file for complete search history.

(56) References Cited

U.S. PATENT DOCUMENTS

| | | |
|---|---|---|
| 4,374,382 A | 2/1983 | Markowitz |
| 4,564,584 A | 1/1986 | Fredericks et al. |
| 5,117,824 A | 6/1992 | Keimel et al. |
| 5,545,186 A | 8/1996 | Olson et al. |
| 5,755,736 A | 5/1998 | Gillberg et al. |
| 7,388,459 B2 | 6/2008 | Receveur et al. |
| 7,809,443 B2 | 10/2010 | Giftakis et al. |
| 7,886,608 B2 | 2/2011 | Mothilal et al. |
| 2007/0179552 A1 | 8/2007 | Dennis et al. |
| 2007/0232023 A1 | 10/2007 | Tong et al. |
| 2008/0205027 A1 | 8/2008 | Coronel et al. |
| 2008/0304999 A1 | 12/2008 | Ishikawa et al. |
| 2009/0278233 A1* | 11/2009 | Pinnington et al. ........... 257/615 |
| 2010/0274221 A1 | 10/2010 | Sigg et al. |
| 2010/0305628 A1 | 12/2010 | Lund et al. |

OTHER PUBLICATIONS (PCT/US2011/034399) PCT Notification of Transmittal of the International Search Report and the Written Opinion of the International Searching Authority.

* cited by examiner

*Primary Examiner* — Seahvosh Nikmanesh
(74) *Attorney, Agent, or Firm* — Carol F. Barry

(57) ABSTRACT

The present disclosure relates to an implantable medical device. The implantable medical device includes a component comprising a first substrate bonded to a second substrate. A method for forming the component includes removing a first portion of tin (Sn) from gold tin (AuSn) through a halogen plasma. A first portion of gold (Au) is exposed in response to removing the first portion of the Sn. The first portion of the Au through a wet etch. A second portion of the Sn is exposed in response to removing the first portion of Au.

18 Claims, 32 Drawing Sheets

GOLD-TIN ETCH USING COMBINATION OF HALOGEN PLASMA AND WET ETCH

CROSS-REFERENCE TO RELATED APPLICATIONS

This application claims the benefit of U.S. Provisional Application No. 61/329,157 filed on Apr. 29, 2010. The disclosure of the above application is incorporated herein by reference in its entirety.

FIELD OF THE DISCLOSURE

The present disclosure relates generally to creating electrical interconnections between materials, and, more particularly, to creating electrical interconnections between materials that are compatible with low temperature hermetic wafer-to-wafer bonds.

BACKGROUND

Implantable medical devices (IMDs) such as implantable pacemakers, implantable cardioverter defibrillator (ICD) devices, cardiac resynchronization therapy defibrillator devices, can detect and deliver therapy for a variety of medical conditions in patients. ICDs typically comprise, inter alia, a control module, a capacitor, and a battery that are housed in a hermetically sealed container with a lead extending therefrom. When therapy is required by a patient, the control module signals the battery to charge the capacitor, which in turn discharges electrical stimuli to tissue of a patient through via electrodes disposed on the lead, e.g., typically near the distal end of the lead.

The control module typically includes one or more hermetically encased integrated circuits (ICs) or chips, which is a miniaturized electronic circuit. An IC is comprised of semiconductor devices (e.g. diode, transistor etc.) and passive components (e.g., transistors, capacitors, resistors, etc.) that are formed in the surface of a thin substrate of semiconductor material. One IC can be connected to another IC or other wafer through wafer to wafer bonds. Wafer to wafer bonds relates to joining major surfaces of the wafers. The joined areas of the wafers creates the hermetic seal(s).

A typical wafer to wafer bond relies on a copper pad disposed on each wafer. The copper pad is higher than the surrounding plane of the wafer. A copper pad on one wafer is aligned with the copper pad on the other wafer. Thermocompression diffusion bonding can be employed to join the copper pads located on each wafer. The ICs are then sealed together with a copper seal ring or a race track near the outer edges of the individual chips. Copper is not biostable and may not provide an adequate seal in vivo. Additionally, copper pads that are coplanar with a thermal oxide can be difficult to planarize and polish. For example, copper and thermal oxide can have different polishing rates. It is therefore desirable to develop new techniques for efficiently and hermetically sealing the electronic circuitry in IMDs. Additionally, a portion of an alloy may need to removed from a substrate before formation of a wafer to wafer bond. Some alloys can only be removed to a certain level and cannot attain a certain level of removal. It is therefore desirable to develop new techniques for efficiently and hermetically sealing the electronic circuitry in IMDs.

SUMMARY

The present disclosure relates to an implantable medical device. The implantable medical device includes a component comprising a first substrate bonded to a second substrate. A method for forming the component includes removing a first portion of tin (Sn) from gold tin (AuSn) through a halogen plasma. A first portion of gold (Au) is exposed in response to removing the first portion of the Sn. The first portion of the Au through a wet etch. A second portion of the Sn is exposed in response to removing the first portion of Au.

DETAILED DESCRIPTION

The present disclosure depicted in FIGS. 6-50 and the accompanying text discloses formation of a wafer to wafer bond and electrical connections that can be used in a variety of implantable medical devices (IMDs) shown in FIGS. 1-5 in which small size, hermeticity and multiple die connection is desired. Sensors and smart leads exemplify the type of components that can implement the teachings of present disclosure.

It will be apparent that elements from one embodiment may be used in combination with elements of the other embodiments, and that the possible embodiments of such apparatus using combinations of features set forth herein is not limited to the specific embodiments shown in the Figures and/or described herein. Further, it will be recognized that the embodiments described herein may include many elements that are not necessarily shown to scale. Further, it will be recognized that the size and shape of various elements herein may be modified but still fall within the scope of the present disclosure, although one or more shapes and/or sizes, or types of elements, may be advantageous over others.

Figure 1:
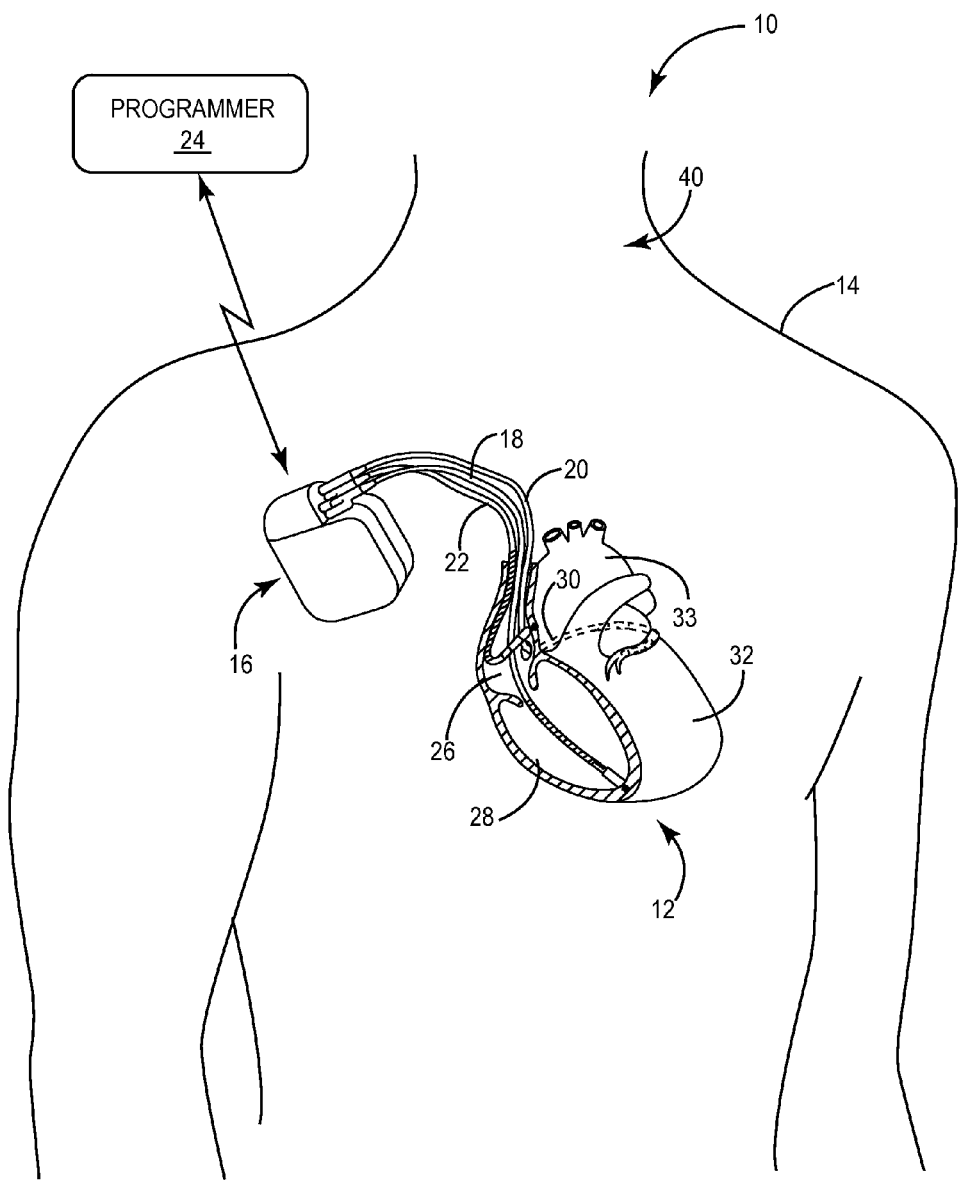
FIG. 1 is a conceptual diagram illustrating an exemplary therapy system including an implantable cardiac device (ICD).

FIG. 1 is a conceptual diagram illustrating an example therapy system 10 that may be used to provide therapy to heart 12 of patient 14. Patient 12 ordinarily, but not necessarily, will be a human. Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22.

Leads 18, 20, 22 extend into the heart 12 of patient 16 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cave, and into the right atrium 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 may be a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, or other clinician, may interact with programmer 24 to communicate with IMD. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or tachyarrhythmia episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20, and 22, or a power source of IMD 16.

The user may use programmer 24 to program a therapy progression, select electrodes used to deliver defibrillation shocks, select waveforms for the defibrillation shock, or select or configure a fibrillation detection algorithm for IMD 16. The user may also use programmer 24 to program aspects of other therapies provided by IMD 14, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
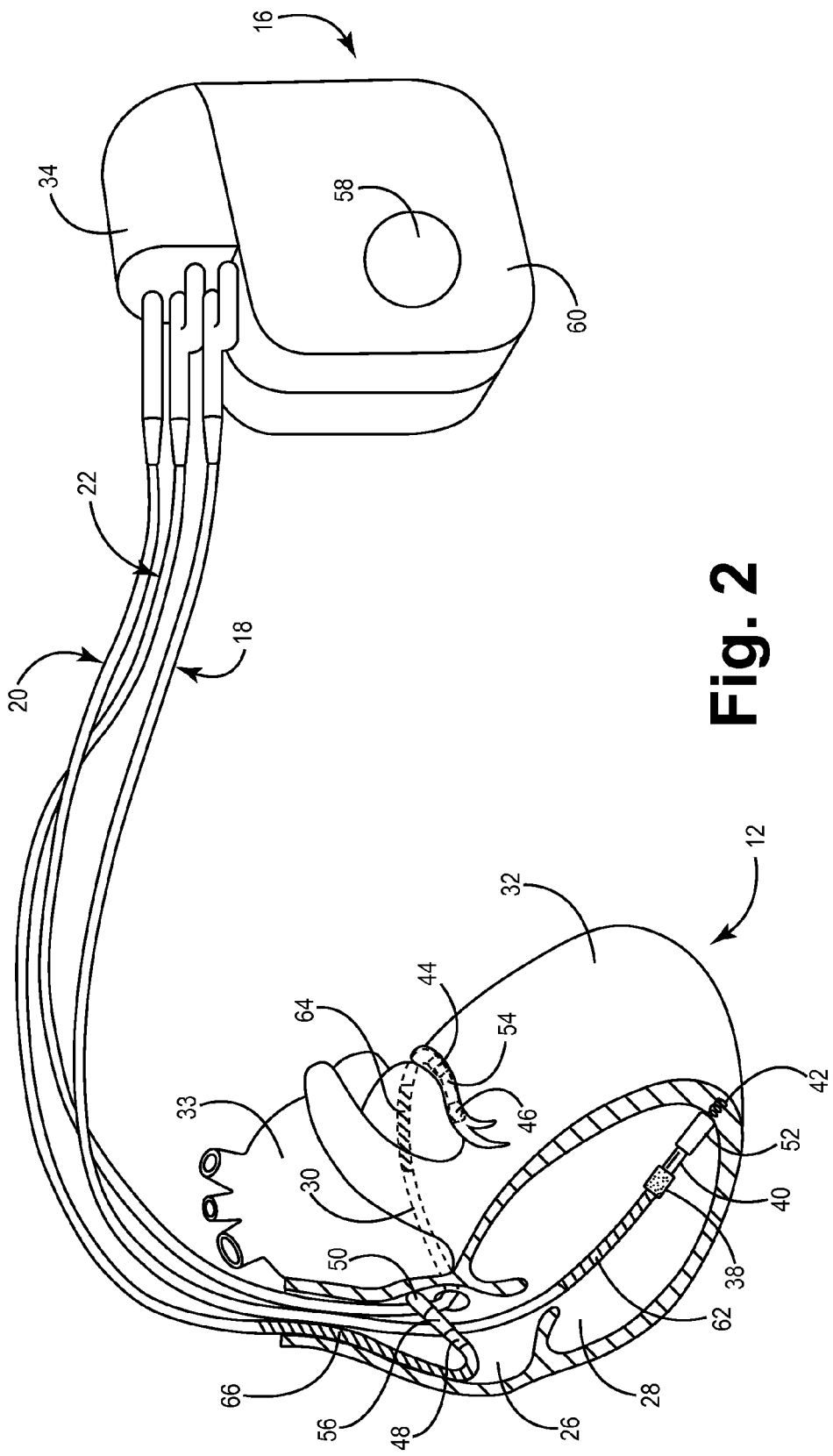
FIG. 2 is a conceptual diagram illustrating the ICD of FIG. 1 and the respective leads in greater detail.

FIG. 2 is a conceptual diagram illustrating IMD 16 and leads 18, 20, 22 of therapy system 10 in greater detail. Leads 18, 20, 22 may be electrically coupled to a stimulation generator, a sensing module, or other modules IMD 16 via connector block 34. In some examples, proximal ends of leads 18, 20, 22 may include electrical contacts that electrically couple to respective electrical contacts within connector block 34. In addition, in some examples, leads 18, 20, 22 may be mechanically coupled to connector block 34 with the aid of set screws, connection pins or another suitable mechanical coupling mechanism.

Each of the leads 18, 20, 22 includes an elongated insulative lead body, which may carry a number of concentric coiled conductors separated from one another by tubular insulative sheaths. In the illustrated example, a pressure sensor 38 and bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 22. In FIG. 2, pressure sensor 38 is disposed in right ventricle 28. Pressure sensor 38 may respond to an absolute pressure inside right ventricle 28, and may be, for example, a capacitive or piezoelectric absolute pressure sensor. In other examples, pressure sensor 38 may be positioned within other regions of heart 12 and may monitor pressure within one or more of the other regions of heart 12, or may be positioned elsewhere within or proximate to the cardiovascular system of patient 14 to monitor cardiovascular pressure associated with mechanical contraction of the heart.

Electrodes 40, 44 and 48 may take the form of ring electrodes, and electrodes 42, 46 and 50 may take the form of extendable helix tip electrodes mounted retractably within insulative electrode heads 52, 54 and 56, respectively. Each of the electrodes 40, 42, 44, 46, 48 and 50 may be electrically coupled to a respective one of the coiled conductors within the lead body of its associated lead 18, 20, 22, and thereby coupled to respective ones of the electrical contacts on the proximal end of leads 18, 20 and 22.

Electrodes 40, 42, 44, 46, 48 and 50 may sense electrical signals attendant to the depolarization and repolarization of heart 12. The electrical signals are conducted to IMD 16 via the respective leads 18, 20, 22. In some examples, IMD 16 also delivers pacing pulses via electrodes 40, 42, 44, 46, 48 and 50 to cause depolarization of cardiac tissue of heart 12. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Any of the electrodes 40, 42, 44, 46, 48 and 50 may be used for unipolar sensing or pacing in combination with housing electrode 58.

As described in further detail with reference to FIG. 4, housing 60 may enclose a stimulation generator that generates cardiac pacing pulses and defibrillation or cardioversion shocks, as well as a sensing module for monitoring the patient's heart rhythm.

Leads 18, 20, 22 also include elongated electrodes 62, 64, 66, respectively, which may take the form of a coil. IMD 16 may deliver defibrillation shocks to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

Pressure sensor 38 may be coupled to one or more coiled conductors within lead 18. In FIG. 2, pressure sensor 38 is located more distally on lead 18 than elongated electrode 62. In other examples, pressure sensor 38 may be positioned more proximally than elongated electrode 62, rather than distal to electrode 62. Further, pressure sensor 38 may be coupled to another one of the leads 20, 22 in other examples, or to a lead other than leads 18, 20, 22 carrying stimulation and sense electrodes. In addition, in some examples, pressure sensor 38 may be self-contained device that is implanted within heart 12, such as within the septum separating right ventricle 28 from left ventricle 32, or the septum separating right atrium 26 from left atrium 33. In such an example, pressure sensor 38 may wirelessly communicate with IMD 16.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation shocks and other therapies to heart 12 via percutaneous leads that extend through the skin of patient 14 to a variety of positions within or outside of heart 12.

In other examples of therapy systems that provide electrical stimulation therapy to heart 12, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 33. As another example, other examples of therapy systems may include a single lead that extends from IMD 16 into right atrium 26 or right ventricle 28, or two leads that extend into a respective one of the right ventricle 26 and right atrium 28. An example of this type of therapy system is shown in AG. 3.

Figure 3:
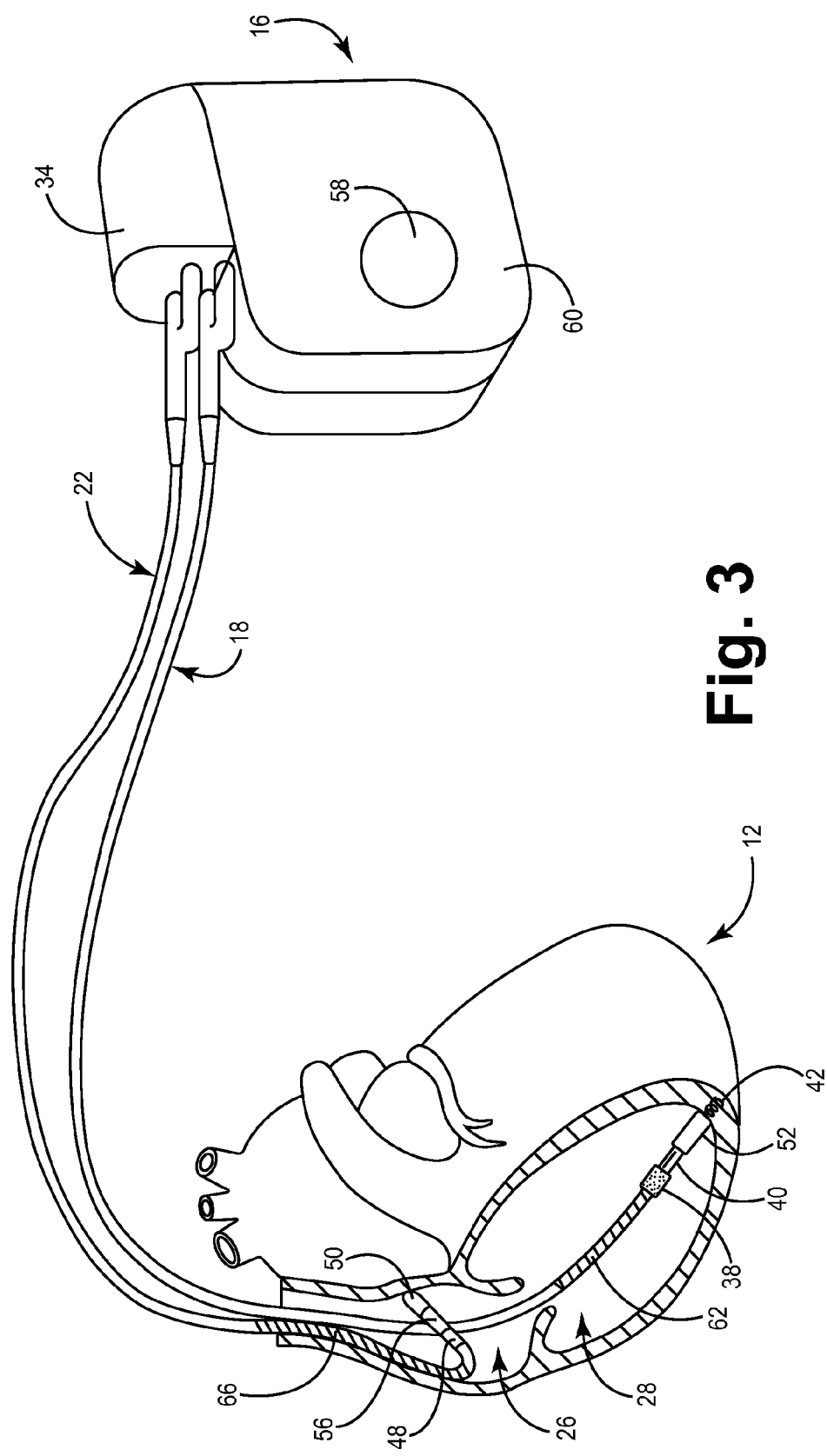
FIG. 3 is a conceptual diagram illustrating the ICD of FIGS. 1 and 2 and the respective leads in greater detail.

FIG. 3 is a conceptual diagram illustrating another example of therapy system 70, which is similar to therapy system 10 of FIGS. 1-2, but includes two leads 18, 22, rather than three leads. Leads 18, 22 are implanted within right ventricle 28 and right atrium 26, respectively. Therapy system 70 shown in AG. 3 may be useful for providing defibrillation and pacing pulses to heart 12.

Figure 4:
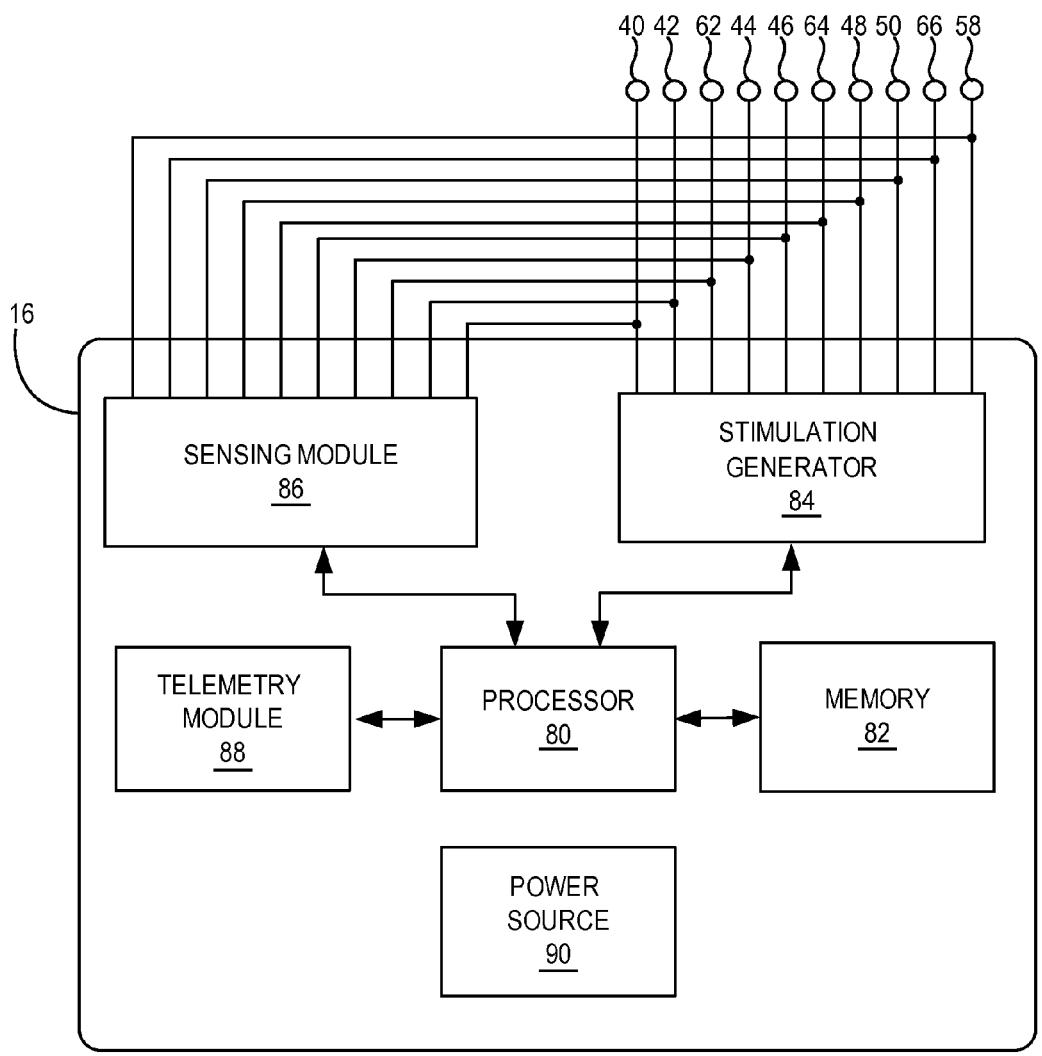
FIG. 4 is a functional block diagram of an example ICD that generates and delivers electrical stimulation to a heart of a patient.

FIG. 4 is a functional block diagram of one example configuration of IMD 16, which includes processor 80, memory 82, stimulation generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. Processor 80 controls stimulation generator 84 to deliver stimulation therapy to heart 12 according to a selected one or more of therapy programs, which may be stored in memory 82. Specifically, processor 44 may control stimulation generator 84 to deliver electrical pulses with the amplitudes, pulse widths, frequency, or electrode polarities specified by the selected one or more therapy programs.

Stimulation generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 80 of IMD 16. Stimulation generator 84 is configured to generate and deliver electrical stimulation therapy to heart 12. For example, stimulation generator 84 may deliver defibrillation shocks to heart 12 via at least two electrodes 58, 62, 64, 66. Stimulation generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, stimulation generator 84 delivers pacing, cardioversion, or defibrillation stimulation in the form of electrical pulses. In other examples, stimulation generator may deliver one or more of these types of stimulation in the form of other signals, such as sine waves, square waves, or other substantially continuous time signals.

Stimulation generator 84 may include a switch module and processor 80 may use the switch module to select, e.g., via a data/address bus, which of the available electrodes are used to deliver defibrillation shocks or pacing pulses. The switch module may include a switch array, switch matrix, multiplexer, or any other type of switching device suitable to selectively couple stimulation energy to selected electrodes.

Sensing module 86 monitors signals from at least one of electrodes 40, 42, 44, 46, 48, 50, 58, 62, 64 or 66 in order to monitor electrical activity of heart 12, e.g., via electrocardiogram (ECG) signals. Sensing module 86 may also include a switch module to select which of the available electrodes are used to sense the heart activity. In some examples, processor 80 may select the electrodes that function as sense electrodes via the switch module within sensing module 86, e.g., by providing signals via a data/address bus. In some examples, sensing module 86 includes one or more sensing channels, each of which may comprises an amplifier. In response to the signals from processor 80, the switch module of within sensing module 86 may couple the outputs from the selected electrodes to one of the sensing channels.

In some examples, one channel of sensing module 86 may include an R-wave amplifier that receives signals from electrodes 40 and 42, which are used for pacing and sensing in right ventricle 28 of heart 12. Another channel may include another R-wave amplifier that receives signals from electrodes 44 and 46, which are used for pacing and sensing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, one channel of sensing module 86 may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing module 86 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an electrogram (EGM). In some examples, the storage of such EGMs in memory 82 may be under the control of a direct memory access circuit. Processor 80 may employ digital signal analysis techniques to characterize the digitized signals stored in memory 82 to detect and classify the patient's heart rhythm from the electrical signals. Processor 80 may detect and classify the heart rhythm of patient 14 by employing any of the numerous signal processing methodologies known in the art.

If IMD 16 is configured to generate and deliver pacing pulses to heart 12, processor 80 may include pacer timing and control module, which may be embodied as hardware, firmware, software, or any combination thereof. The pacer timing and control module may comprise a dedicated hardware circuit, such as an ASIC, separate from other processor 80 components, such as a microprocessor, or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module within processor 80 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals from sensing module 86 to blank one or more channels, e.g., amplifiers, for a period during and after delivery of electrical stimulation to heart 12. The durations of these intervals may be determined by processor 80 in response to stored data in memory 82. The pacer timing and control module of processor 80 may also determine the amplitude of the cardiac pacing pulses.

During pacing, escape interval counters within the pacer timing/control module of processor 80 may be reset upon sensing of R-waves and P-waves. Stimulation generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 80 may reset the escape interval counters upon the generation of pacing pulses by stimulation generator 84, and thereby control the basic timing of cardiac pacing functions, including anti-tachyarrhythmia pacing.

The value of the count present in the escape interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as ventricular fibrillation event or ventricular tachycardia event. Upon detecting a threshold number of tachyarrhythmia events, processor 80 may identify the presence of a tachyarrhythmia episode, such as a ventricular fibrillation episode, a ventricular tachycardia episode, or a non-sustained tachycardia (NST) episode.

In some examples, processor 80 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 80 and any updating of the values or intervals controlled by the pacer timing and control module of processor 80 may take place following such interrupts. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson at al., entitled, "PRIORITIZED RULE BASED METHOD AND APPARATUS FOR DIAGNOSIS AND GREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al, and U.S. Pat. No. 5,755,736 to Gillberg et al. are incorporated herein by reference in their entireties. However, other arrhythmia detection methodologies may also be employed by processor 80 in other examples.

In the examples described herein, processor 80 may identify the presence of an atrial or ventricular tachyarrhythmia episode by detecting a series of tachyarrhythmia events (e.g., R-R or P-P intervals having a duration less than or equal to a threshold) of an average rate indicative of tachyarrhythmia or an unbroken series of short R-R or P-P intervals. The thresholds for determining the R-R or P-P interval that indicates a tachyarrhythmia event may be stored within memory 82 of IMD 16. In addition, the number of tachyarrhythmia events that are detected to confirm the presence of a tachyarrhythmia episode may be stored as a number of intervals to detect (N ID) threshold value in memory 82. In some examples, processor 80 may also identify the presence of the tachyarrhythmia episode by detecting a variable coupling interval between the R-waves of the heart signal. For example, if the interval between successive tachyarrhythmia events varies by a particular percentage or the differences between the coupling intervals are higher than a given threshold over a predetermined number of successive cycles, processor 80 may determine that the tachyarrhythmia is present.

If processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by stimulation generator 84 may be loaded by processor 80 into the pacer timing and control module to control the operation of the escape interval counters therein and to define refractory periods during which detection of R-waves and P-waves is ineffective to restart the escape interval counters.

If IMD 16 is configured to generate and deliver defibrillation shocks to heart stimulation generator 84 may include a high voltage charge circuit and a high voltage output circuit. In the event that generation of a cardioversion or defibrillation shock is required, processor 80 may employ the escape interval counter to control timing of such cardioversion and defibrillation shocks, as well as associated refractory periods. In response to the detection of atrial or ventricular fibrillation or tachyarrhythmia requiring a cardioversion pulse, processor 80 may activate a cardioversion/defibrillation control module, which may, like pacer timing and control module, be a hardware component of processor 80 and/or a firmware or software module executed by one or more hardware components of processor 80. The cardioversion/defibrillation control module may initiate charging of the high voltage capacitors of the high voltage charge circuit of stimulation generator 84 under control of a high voltage charging control line.

Processor 80 may monitor the voltage on the high voltage capacitor, e.g., via a voltage charging and potential (VCAP) line. In response to the voltage on the high voltage capacitor reaching a predetermined value set by processor 80, processor 80 may generate a logic signal that terminates charging. Thereafter, timing of the delivery of the defibrillation or cardioversion pulse by stimulation generator 84 is controlled by the cardioversion/defibrillation control module of processor 80. Following delivery of the fibrillation or tachycardia therapy, processor 80 may return stimulation generator 84 to a cardiac pacing function and await the next successive interrupt due to pacing or the occurrence of a sensed atrial or ventricular depolarization.

Stimulation generator 84 may deliver cardioversion or defibrillation shocks with the aid of an output circuit that determines whether a monophasic or biphasic pulse is delivered, whether housing electrode 58 serves as cathode or anode, and which electrodes are involved in delivery of the cardioversion or defibrillation shocks. Such functionality may be provided by one or more switches or a switching module of stimulation generator 84.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac episodes that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

The various components of IMD 16 are coupled to power source 90, which may include a rechargeable or non-rechargeable battery. A non-rechargeable battery may be selected to last for several years, while a rechargeable battery may be inductively charged from an external device, e.g., on a daily or weekly basis.

Figure 5:
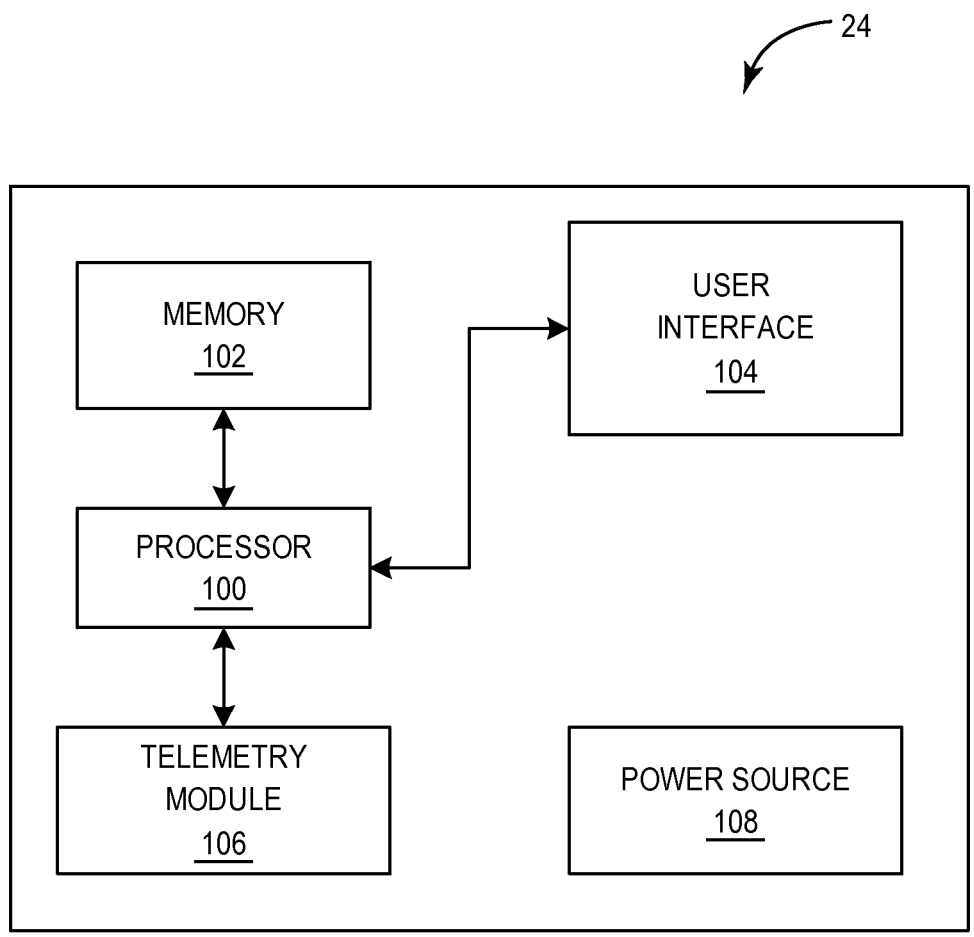
FIG. 5 is a functional block diagram of an example medical device programmer.

FIG. 5 is block diagram of an example programmer 24. As shown in FIG. 5, programmer 24 includes processor 100, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 104, which may include display to present graphical user interface to a user, and a keypad or another mechanism for receiving input from a user.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Memory 102 may store instructions. For example, read only memory (ROM) stores computer instructions. Processor 80 is configured to access the computer instructions from ROM and then processor 80 executes the computer instructions. Execution of computer instructions by processor 80 can cause processor 100 to generate control signals to components of the IMD 16 or components electrically and/or mechanically coupled to IMD 16. Processor 80 can provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient. Memory 102 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 102, which may be coupled to an internal antenna or an external antenna. An external antenna that is coupled to programmer 24 may correspond to the programming head that may be placed over heart 12, as described above with reference to FIG. 1. Telemetry module 102 may be similar to telemetry module 88 of IMD 16 (FIG. 4).

Telemetry module 102 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g.; according to the IrDA standard, or other standard or proprietary telemetry protocols. In this manner, other external devices may be capable of communicating with programmer 24 without needing to establish a secure wireless connection.

Power source 108 delivers operating power to the components of programmer 24. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 104 may include circuitry to monitor power remaining within a battery. In this manner, user interface 104 may provide a current battery level indicator or low battery level indicator when the battery needs to be replaced or recharged. In some cases, power source 108 may be capable of estimating the remaining time of operation using the current battery.

Referring again to FIG. 4, processor 80 of IMD 16 may detect a tachyarrhythmia episode, such as a ventricular fibrillation, ventricular tachycardia, fast ventricular tachyarrhythmia episode, or a NST episode, based on electrocardiographic activity of heart 12 that is monitored via sensing module 86. For example, sensing module 86, with the aid of at least some of the electrodes 40, 42, 44, 46, 48, 50, 58, 62, 64, and 66 (shown in FIGS. 1-2), may generate an electrocardiogram (ECG) or electrogram (EGM) signal that indicates the electrocardiographic activity. Alternatively, sensing module 86 may be coupled to sense electrodes that are separate from the stimulation electrodes that deliver electrical stimulation to heart 12 (shown in FIGS. 1-3), and may be coupled to one or more different leads than leads 18, 20, 22 (shown in FIGS. 1-2). The ECG signal may be indicative of the depolarization of heart 12.

For example, as previously described, in some examples, processor 80 may identify the presence of a tachyarrhythmia episode by detecting a threshold number of tachyarrhythmia events (e.g., R-R or P-P intervals having a duration less than or equal to a threshold). In some examples, processor 80 may also identify the presence of the tachyarrhythmia episode by detecting a variable coupling interval between the R-waves of the heart signal.

The techniques described in this disclosure, including those attributed to IMD 16, programmer 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

Presented in FIGS. 6-50 and the accompanying text is a series of operations performed on a wafer in order to form a hermetic wafer to wafer bond. Table presented below briefly summarizes each operation relative to each figure.

Figure 6:
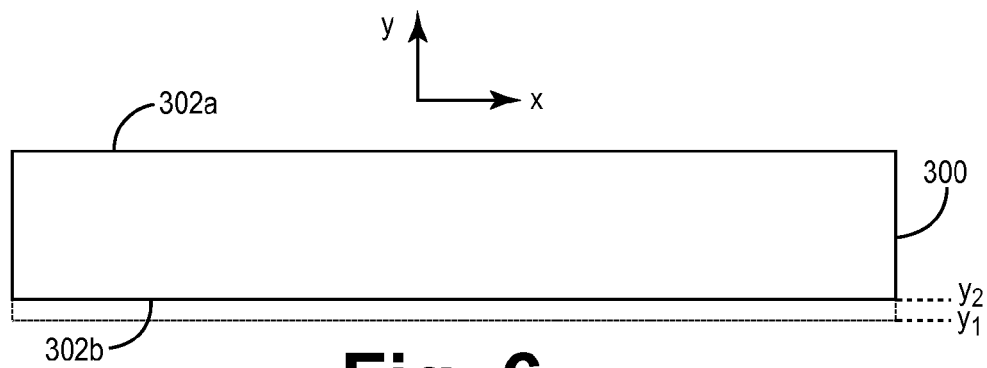
FIG. 6 depicts a schematic view of a substrate that has undergone a grinding operation.

Referring to FIG. 6, a substrate 300, also referred to as a wafer, is obtained and placed in position to undergo multiple sequential processing operations that can be automated. The substrate 300 is typically comprised of a silicon crystal, commonly referred to as single crystal silicon or a glass composition. An exemplary glass composition can include borosilicate glass (BSG) commercially available from Plan Optik located in Elsoff, Germany. Substrate 300 includes a front side 302a (first side or topside) and a backside 302b (second side or bottom side). The back side 302b is depicted horizontally along the x-axis while the top side 302a is depicted vertically higher along the y-axis than back side 302b and parallel to backside 302b. The front and backsides 302a,b undergo a series of operations in preparation for patterning of front and backsides 302a,b.

Backside 302b of the silicon substrate 300 is shown to have undergone a grinding operation so that the backside 302b can receive a scribe, which identifies the wafer as being produced by a particular operation. Preferably, about $\Delta y$ (y2−y1) which is about 1.5 mil of silicon is removed from backside 302b during the grinding operation; however, skilled artisans appreciate that the amount of silicon removed can be adjusted. For example, an increased amount or decreased amount of silicon can be removed depending on the final desired characteristic of backside 302b that undergoes the grinding operation. Grinding equipment manufactured by DISCO, located in Japan can be used to grind a portion of the silicon from backside 302b.

Figure 7:
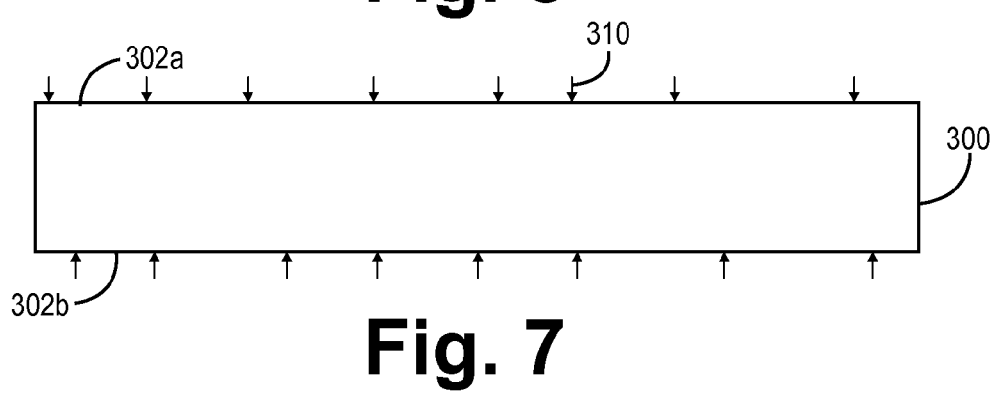
FIG. 7 depicts a schematic side view of the substrate of FIG. 6 that has undergone a cleaning operation.

After completion of the grinding operation, the substrate 300 is then loaded into a substrate mover, also referred to as a TEFLON® boat, so that the substrate can be moved into position for a cleaning operation. The substrate mover is configured to hold and move substrate 300 along an x-axis and/or a y-axis direction during the cleaning operation. For example, at operation 2, substrate 300 is placed in a substrate mover which is then positioned into cleaning equipment. The cleaning equipment includes a cleaning spray 310 in which compound(s) are sprayed onto the substrate 300 as shown in FIG. 7 while substrate 300 is rotated about the x-axis. The cleaning equipment is commercially available under the trade name Mercury from FSI equipment located in Chaska, Minn. Hydrogen peroxide ($H_2O_2$)/ammonium hydroxide ($NH_4OH$) and/or $H_2O_2$/hydrochloric acid (HCl) can be used as the cleaning spray 310 or as a part of the cleaning spray 310 for cleaning substrate 300. Substrate 300 is considered sufficiently cleaned once particulate matter, organic, ionic, and/or metallic impurities are removed from surfaces 302a,b of substrate 300.

Figure 8:
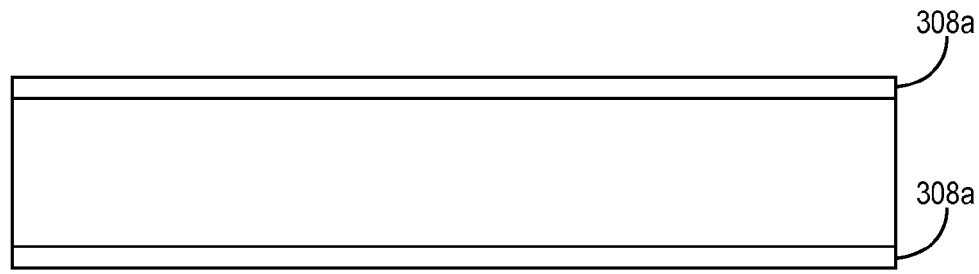
FIG. 8 depicts a schematic side view of a thermal oxide formed on the front and backsides of the substrate shown in FIG. 7.

After the substrate 300 has been cleaned, barrier layers 308a are formed on substrate 300 as shown in FIG. 8 in order to protect silicon 300 while a scribe is placed on the backside 302b. To form barrier layer 308a, substrate 300 is placed into a substrate mover such as a silicon carbide boat which is configured to withstand high temperatures. The silicon carbide boat, carrying substrate 300, is pushed into a horizontal diffusion furnace while gases (oxygen $O_2$ (4 slm) and/or $H_2$) are introduced to the thermal processing chamber. The thermal processing chamber of a diffusion furnace is under atmospheric pressure and a temperature at about 1000° C. The diffusion furnace is commercially available from MRL Industries located in Sonora, Calif. After a portion of the silicon has been oxidized to form barrier layer 308a, the gases (oxygen $O_2$ (4 slm) and/or $H_2$) are turned off and the silicon carbide boat is moved out of the thermal processing chamber. Barrier layer 308a, also referred to as a thermal oxide layer, such as silicon dioxide, is formed over a top side 302a and a backside 302b of substrate 300 in order to protect the wafer while undergoing scribing at operation 4. As shown, barrier layer 308a has a thickness of about 5,000 angstroms (Å). The barrier layer 308a can range in thickness from about 4,000 Å to about 30,000 Å. In one or more embodiments, the thickness of the barrier layer 308a is preferably about 15000 angstrom (Å).

Figure 9:
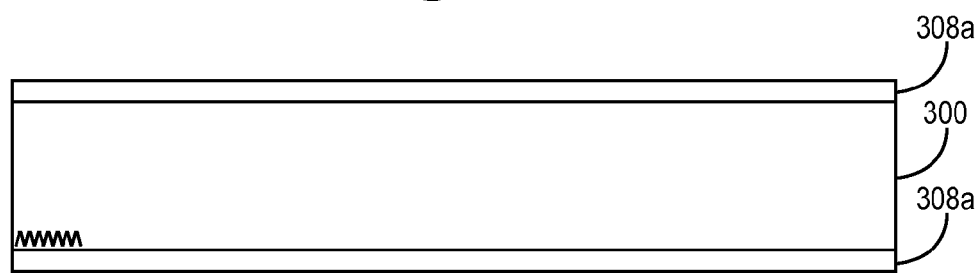
FIG. 9 depicts a schematic side view of a backside of the substrate of FIG. 8 in which a scribe is formed in the backside.

At operation 4, the silicon substrate 300 receives a scribe 306 typically on the backside 302b, as shown in FIG. 9. Scribing substrate 300 allows the wafer to be tracked through the remainder of the processing steps. A scribe 306 is preferably used on the backside 302b to avoid particles and contaminants from collecting in the scribed area during, for example, a deposition step, thereafter spreading to other areas of the wafer during subsequent processing steps. Additionally, referring briefly to FIG. 45, since front side 402 of first substrate 300a is bonded to front side 402 of second substrate 300b, the only way to visually detect each scribe 306 is to ensure scribe 306 is placed on back side 302b of each wafer.

Figure 10:
FIG. 10 depicts a schematic side view of the substrate of FIG. 9 in which thermal oxide is removed therefrom.

At operation 5 shown in FIG. 10, barrier layer 308 is removed from substrate 300 through a stripping operation. To strip barrier layer 308 from substrate 300, the substrate 300 is placed into another substrate mover such as a TEFLON® boat. The TEFLON® boat securely holds and moves substrate 300 through a container of stripper until the barrier layer 308 is removed and silicon is exposed at the surface of the front and backsides 302a,b. For example, the TEFLON® boat can be placed into a container of stripping solution such as hydrofluoric acid (HF) for about a minute to remove barrier layer 308.

Figure 11:
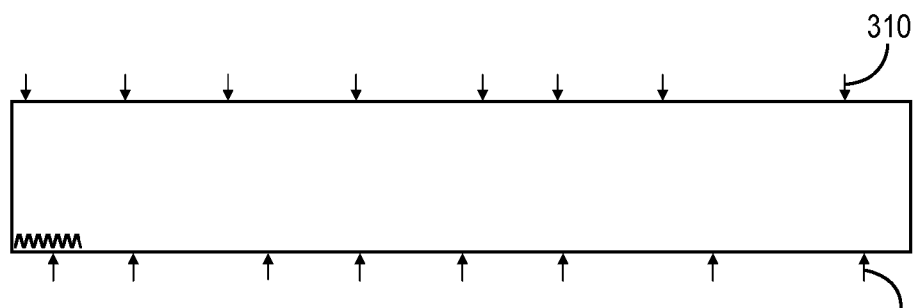
FIG. 11 depicts a schematic side view of the substrate of FIG. 10 that has undergone a cleaning operation.

At operation 6 shown in FIG. 11, the first and second sides 302a,b of substrate 300 is cleaned through a wet chemical cleaning operation such as that which was previously described relative to operation 2. Cleaning spray 310 comprising $H_2O_2/NH_4OH$ and/or $H_2O_2/HCl$ is used to clean the first and second sides 302a,b. Substrate 300 is then removed from the TEFLON® boat and placed into a silicon carbide mover or boat in preparation for moving the substrate 300 into the thermal processing chamber of the diffusion furnace.

Figure 12:
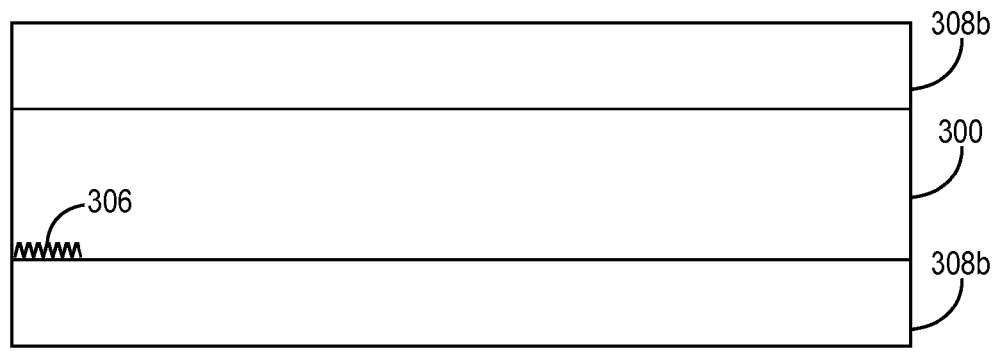
FIG. 12 depicts a schematic side view of thermal oxide formed over the substrate shown in FIG. 11.

At operation 7 shown in FIG. 12, first and second barrier layers 308b (also referred to as thermal oxide layers) are formed on the first and second sides 302a,b of substrate 300. First and second barrier layers 308b are grown over first and second sides 302a,b through a wet thermal oxidation process as previously described. Wet thermal oxidation is performed at, for example, 1200° C. for about three hours while $O_2$ and $H_2$ are continuously introduced into the thermal chamber of the diffusion furnace. As depicted in FIG. 12, barrier layer 308b has a thickness of about 15,000 Å.

Figure 13:
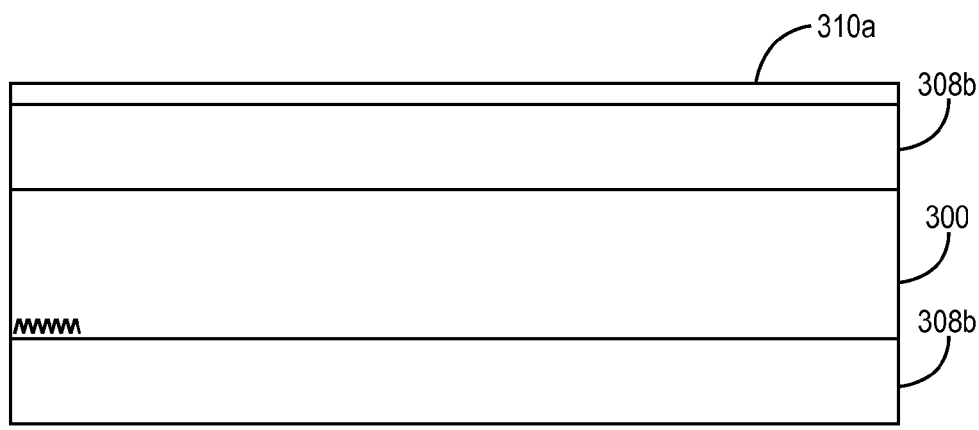
FIG. 13 depicts a schematic side view of photoresist deposited over the thermal oxide shown in FIG. 12.

At operation 8 shown in FIG. 13, an excess amount of photoresist 310a is introduced to or placed onto barrier layer 308b. For example, a technique referred to as spin coating can be used to form a thin uniform layer of photoresist 310a on the first side 302a of substrate 300. Substrate 300 is secured inside a spin coater, which is then rotated at high speed in order to spread the fluid by centrifugal force. Rotation is continued while the excess photoresist 310a spins off the edges of the substrate 300 and until the desired thickness of the film is achieved. The thickness of the photoresist 310a can depend on the viscosity of the photoresist 310a, the volatility of the photoresist 310a, and/or the angular speed of spinning the substrate 300 in the spin coater. Photoresist 310a thickness is nominally about 1.5 microns.

In this example, a positive photoresist 310a is employed. An exemplary positive photoresist is commercially available as SPR3010 photoresist from Rohm and Hass located in Philadelphia, Pa. and now a wholly owned subsidiary of Dow Chemical Company.

Figure 14:
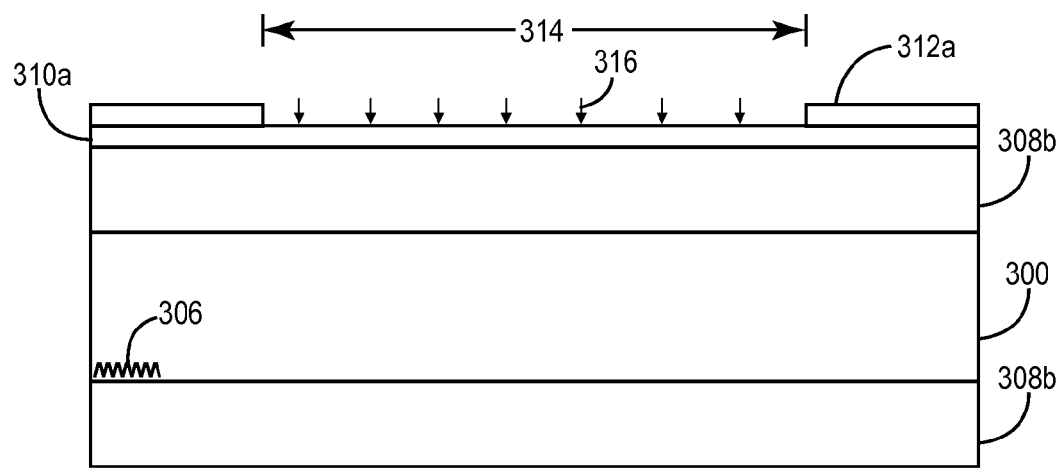
FIG. 14 depicts a schematic side view of a mask placed over the photoresist shown in FIG. 13.
Figure 15:
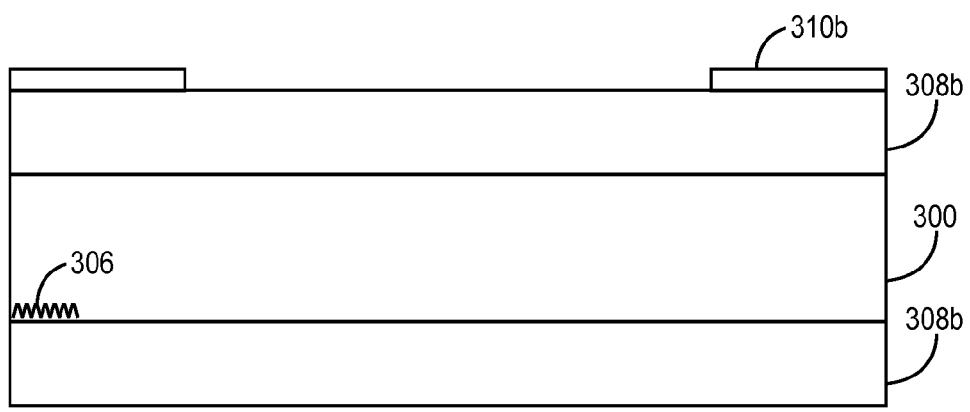
FIG. 15 depicts a schematic side view of exposed photoresist removed from a thermal oxide layer shown in FIG. 14.

At operation 9 shown in FIG. 14, a mask 312a is placed and aligned over the positive photoresist 310a. Mask 312a, manually loaded into its fixture, includes continuous opaque areas that block or cover predetermined areas of the photoresist 310a and apertures 314 that allow photoresist 310a to be exposed to ultraviolet (UV) light 316 through a UV light aperture (not shown), UV light 316 contacts the photoresist 310b which makes the photoresist 310b soluble to an aqueous developer solution. An exemplary developer solution can be a MF26A developer, commercially available from Rohm and Hass. At operation 10 shown in FIG. 15, the developer solution (not shown) is introduced over the photoresist 310b that was exposed to UV light 316. For example, the developer solution is spun onto the substrate 300 through the spin coating technique previously described. After the developer solution washes over the photoresist 310a that was exposed to the UV light 316, the exposed photoresist 310b is removed. Specifically, the exposed photoresist 310b spins-off due to the centrifugal force applied to substrate 300 while substrate 300 continuously rotates about the y-axis, which is the vertical axis relative to the ground, in the spin coater. Substrate 300 is then moved to an etch processing chamber, referred to as a Rainbow model etcher, commercially available from Lam Research Corporation located in Fremont, Calif.

Figure 16:
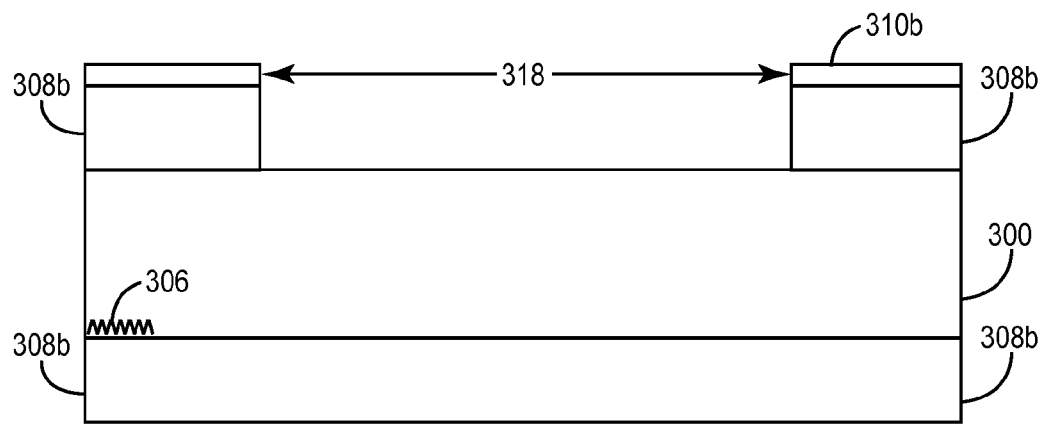
FIG. 16 depicts a schematic side view of an exposed thermal oxide removed from FIG. 15.

At operation 11 shown in FIG. 16, a portion of the barrier layer 308 is etched away through a plasma reactive ion etch (RIE) thereby forming a via 318. Via 318 is typically about 5 to 20 microns in diameter and possesses a height of about 0.1 to 1 micron. Dry etching involves applying or introducing plasma to the surface of substrate 300 such that the plasma strikes and etches the surface of substrate 300. Plasma includes reactive gases such as carbon tetrafluoride ($CF_4$) with the addition of ionized gasses such as nitrogen, argon, and/or helium or other suitable gases.

Figure 17:
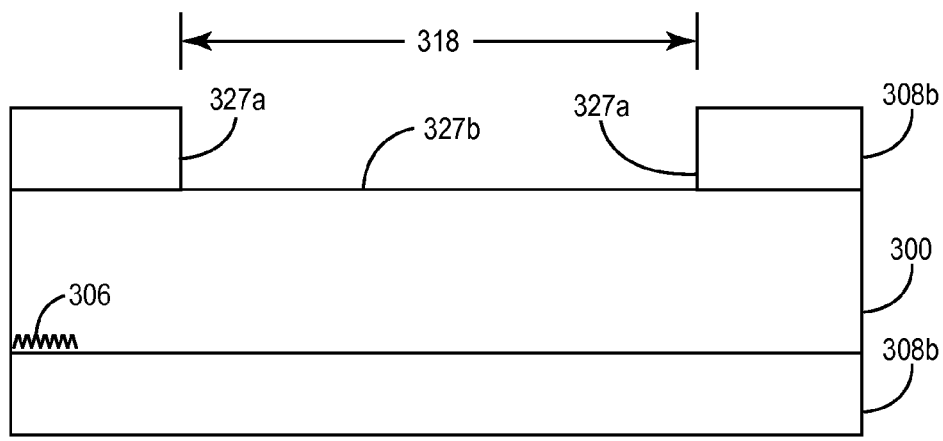
FIG. 17 depicts the remaining portion of photoresist was removed as compared to the substrate depicted in FIG. 16.
Figure 18:
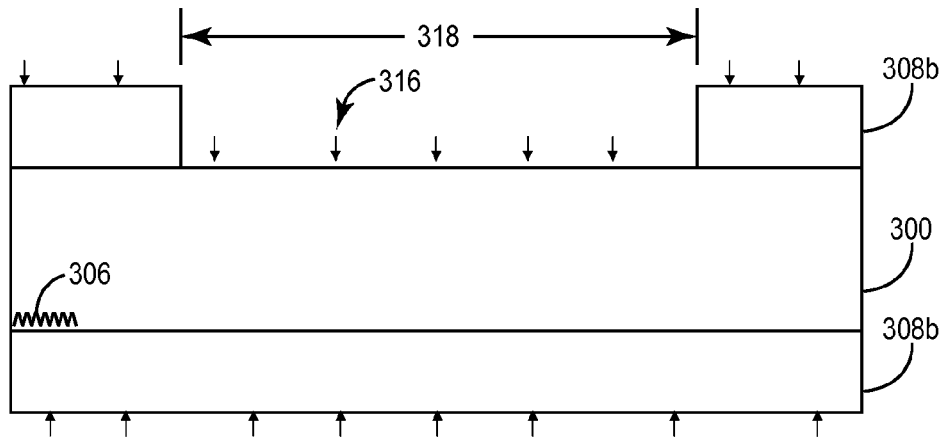
FIG. 18 depicts the substrate of FIG. 17 undergoing a cleaning operation.

At operation 12 shown in FIG. 17, the remaining photoresist 310b is stripped from the top surface 302a of substrate 300 through the use of ionized oxygen plasma stripping operation until the exposed photoresist 310b is removed. The oxygen plasma attacks and etches away the organic material (e.g. photoresist) but does not affect the inorganic material (e.g. silicon etc.). The stripper processing chamber, under a low pressure vacuum (e.g. 1.5 Torr), continuously removes etched volatilized particles away. The stripper processing chamber in stripping equipment is commercially available from Matrix located in Richmond, Calif.

Thereafter, substrate 300 is moved to the TEFLON® substrate 300 mover so that substrate 300 can undergo yet another cleaning operation. At operation 13 shown in FIG. 18, a wet chemical is used to clean substrate 300 as similarly described relative to operations 2 and 6. Exemplary cleaning compounds for operation 13 include $H_2O_2/NH_4OH$ and/or $H_2O_2/HCl$.

Figure 19:
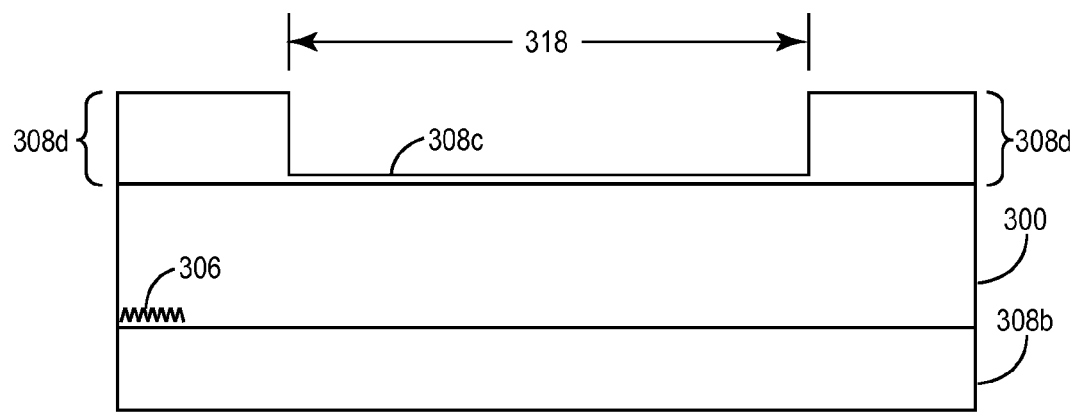
FIG. 19 depicts thermal oxide formed over the substrate of FIG. 18.
Figure 20:
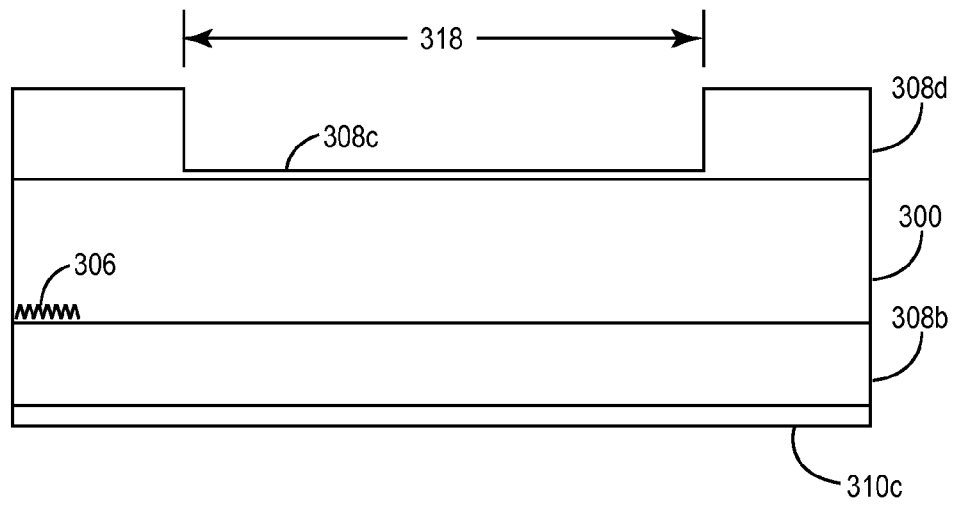
FIG. 20 depicts photoresist being applied to the backside of the substrate shown in FIG. 19.

At operation 14 shown in FIG. 19, first and second barrier layer 308c,d are formed on the first and second sides 302a,b of substrate 300, as previously described relative to operations 3 and 7 except the processing conditions are different. To illustrate, wet thermal oxidation is performed at, for example, 1,000° C. for about 30 minutes while $O_2$ and $H_2$ are continuously introduced into the thermal chamber of the diffusion furnace. As depicted in FIG. 19, barrier layer 308c,d has a thickness of about 2,000 Å.

Optional operations 15-19, shown in FIGS. 20-24, form vias 324, 314b in the backside 302b of substrate 300 in order to form alignment features to align the first and the second wafers (also referred to as the first and second substrates 300a, b, respectively) together prior to the bonding operation between the first and second wafers. At operation 15 shown in FIG. 20, a photoresist 310c is applied through spin coating over the backside 302b of substrate 300. An exemplary positive photoresist is commercially available as SPR3010 photoresist from Rohm and Hass located in Philadelphia, Pa. and a wholly owned subsidiary of Dow Chemical Company. Substrate 300 is positioned onto a hot plate upon which the substrate 300 is exposed to a short soft bake to harden the photoresist 310c and drive out volatile components.

Soft baking can occur at a temperature of about 95 degrees Celsius for about 60 seconds. Soft-baking helps in photo-imaging and to remove any residual solvents from the photoresist 310c.

Figure 21:
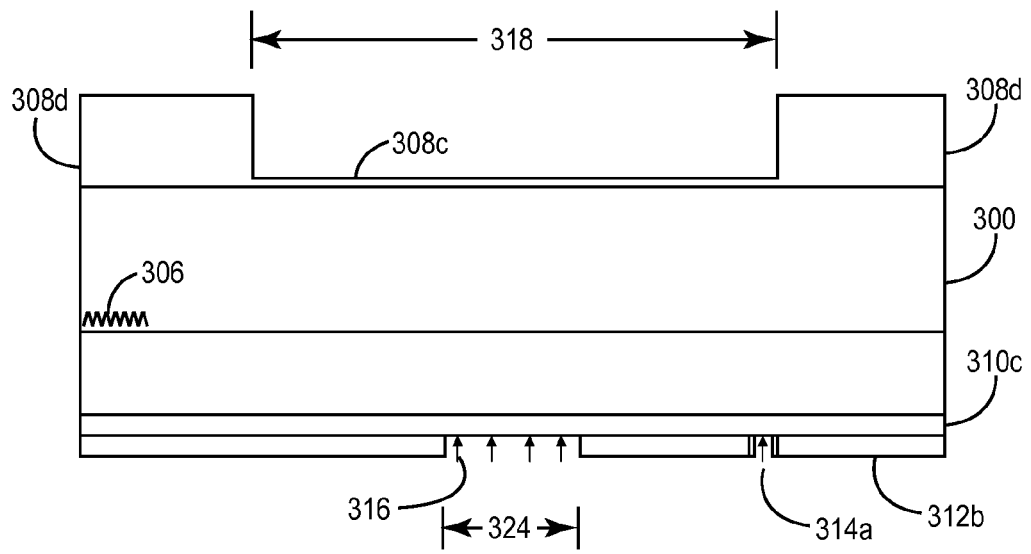
FIG. 21 depicts a mask placed over the photoresist which resides of the backside of the substrate shown in FIG. 20.
Figure 22:
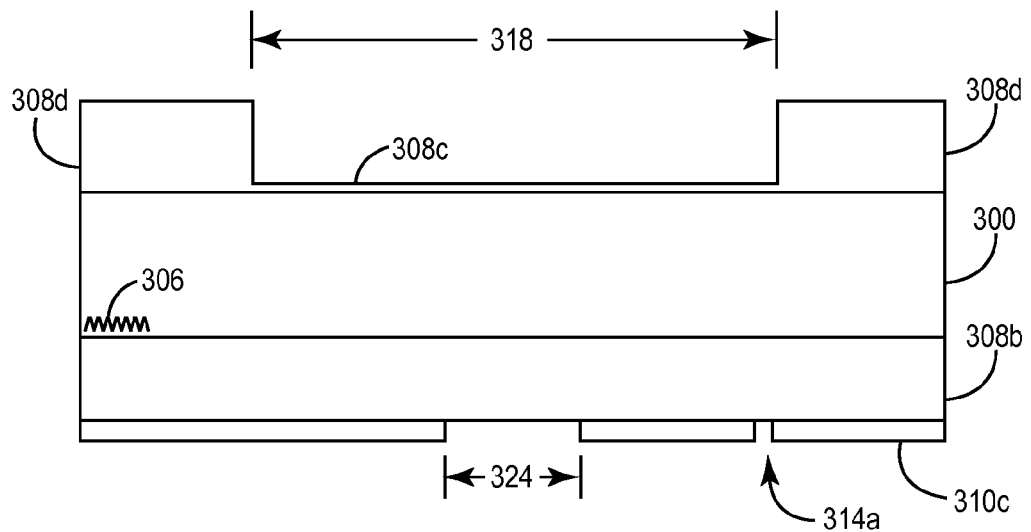
FIG. 22 depicts exposed photoresist removed from the substrate shown in FIG. 21.
Figure 23:
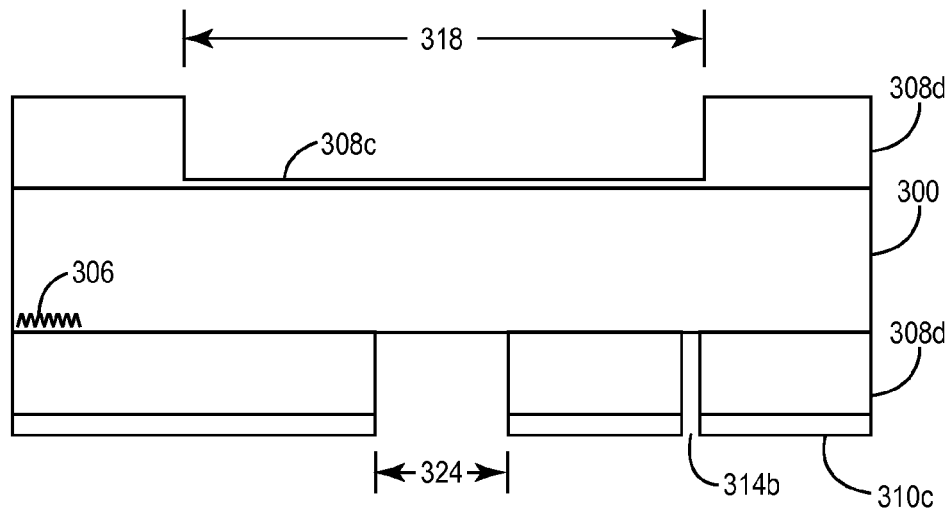
FIG. 23 depicts vias formed in the thermal oxide of the substrate shown in FIG. 22.
Figure 24:
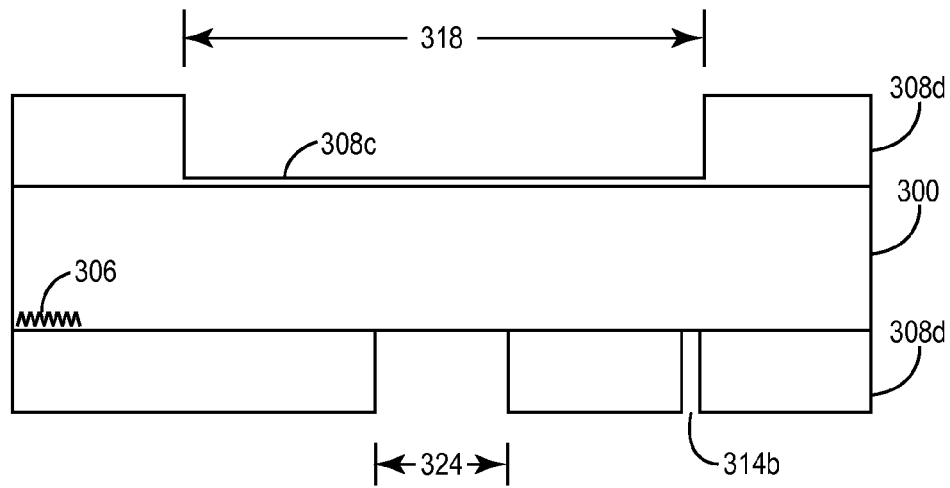
FIG. 24 depicts photoresist being removed from the thermal oxide on the substrate shown in FIG. 23.

At operation 16 shown in FIG. 21, a mask 312b is placed over photoresist 310c. Similar to operation 9, areas of the photoresist 310c are exposed through the mask 312b. At operation 17 shown in FIG. 22, a developer removes exposed photoresist 310c through spinning of the substrate 300 in a spin coater. Vias 314a, 324a are formed in photoresist 310c after the exposed photoresist 310c is removed. At operation 18 shown in FIG. 23, backside 302b is dry etched in an Lam 4520 dry etcher. Plasma with carbon tetrafluoride (CF4)) is used to etch thermal oxide 308d. Plasma with nitrogen trifluoride (NF3) is used to etch thermal oxide 308d. At operation 19 shown in FIG. 24, photoresist 310c is removed from thermal oxide 308d, through oxygen plasma RIE stripping operation as previously described.

Figure 25:
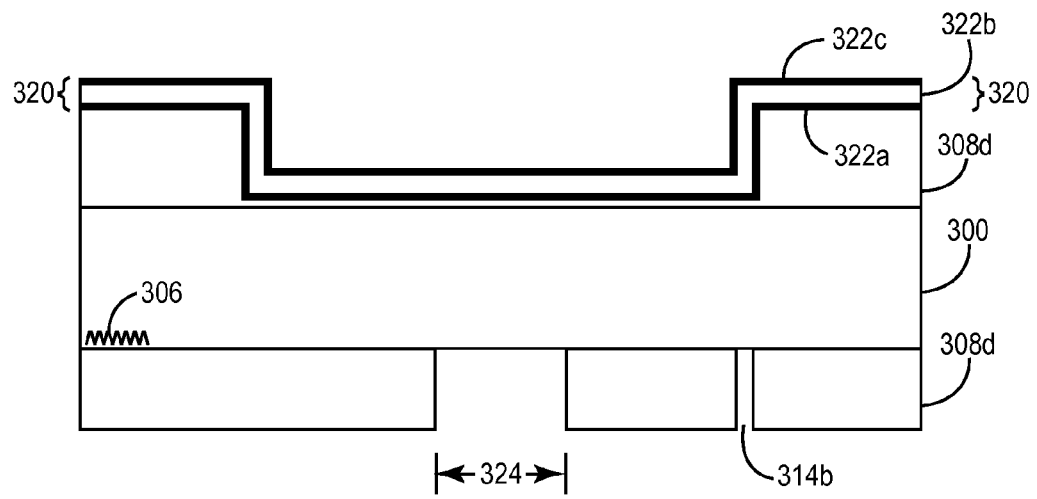
FIG. 25 depicts a pad formed of first, second and third conductive materials deposited in a via located in thermal oxide on a frontside of the substrate shown in FIG. 24.

At operation 20 shown in FIG. 25, conductive pad 320, comprising adhesion material, is formed through metal and/or alloy deposition. Metal and/or alloy deposition occurs in the via 318 and along the surface of thermal oxide 308d. Adhesion material can be multilayered and comprise transition metal elements such as chromium and/or titanium (Ti) along with an optional barrier metal such as platinum (Pt) and/or nickel (Ni) and a wettable layer such as gold.

A wide variety of ways can be employed to deposit the metal or alloy into a via 318 such as sputter deposition. For example, a first conductive material 322a such as Ti can be deposited into via 318. The first conductive material 322a such as Ti can have a thickness of about 300 Å. Thereafter, a second conductive material 322b such as gold (Au) can be introduced or deposited over the first conductive material 322a. The second conductive material 322b such as Au can have a thickness of about 5,000 Å. A third conductive material 322c such as chromium (Cr) can be introduced over the second conductive material 322b. For example, Cr can be deposited to a thickness of about 300 Å over the second conductive material 322b. In one or more embodiments, Cr is deposited over the second conductive material 322b through sputtering in which argon is employed. Sputter processes can occur over the wafer at temperatures up to 300 C. The vacuum chamber pressure is typically pumped to $1 \times 10^{-7}$ Torr before sputtering begins, and during the processing of argon, pressure is typically 3 to 10 milliTorr. In one or more other embodiments, a thinner layer of second conductive material 322b (e.g. gold etc.) can be formed. For example, the gold material can be about 1000 Å thick. In one or more other embodiments, first, second, and third conductive materials 322a-c can comprise titanium, platinum, and titanium (Ti/Pt/Ti) material, respectively. In one or more embodiments, a preferable thickness is about 300 Å Ti, about 2000 Å Pt, and 300 Å Ti.

In one or more other embodiments pad 320 can employ nickel vanadium (NiV)/Au/Ti as third conductive material 322c, second conductive material 322b, first conductive material 322a, respectively.

In one or more other embodiments, it is appreciated that pad 320 can be formed of four or more conductive materials. For example, pad 320 can comprise Ti/Pt/Au/Ti in which fourth conductive material (not shown in FIG. 25) is Ti which is deposited on third conductive material 322c. Third conductive material 322c is Ni. Second conductive material 322b is Au. First conductive material 322a is Ti.

In one or more other embodiments, it is appreciated that pad 320 can be formed of four or more conductive materials. For example, pad 320 can comprise Ti/Ni/Au/Ti in which fourth conductive material (not shown in FIG. 25) is Ti which is deposited on third conductive material 322c. Third conductive material 322c is Ni. Second conductive material 322b is Au. First conductive material 322a is Ti.

Figure 26:
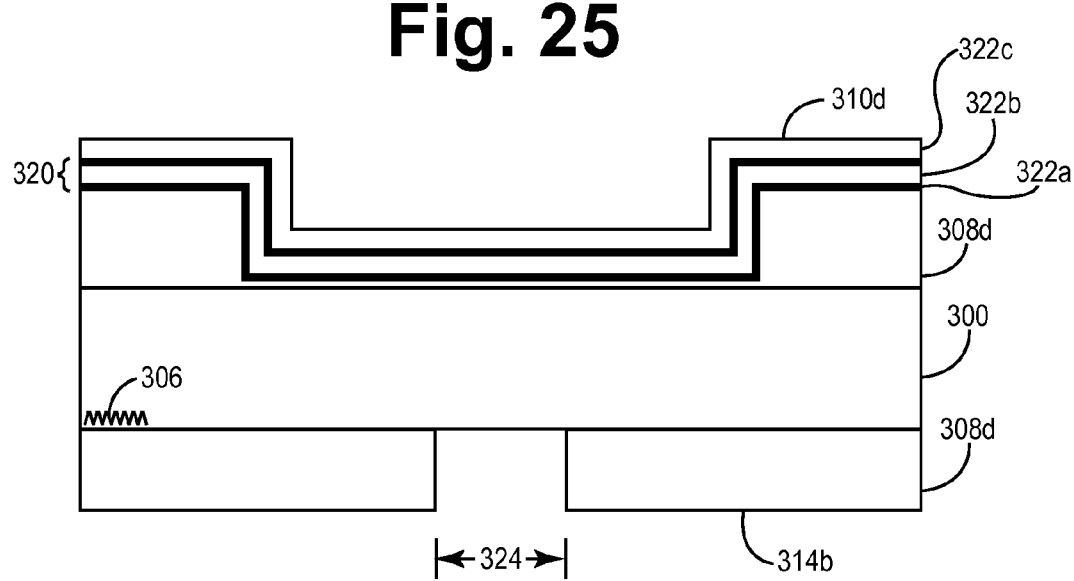
FIG. 26 depicts photoresist deposited over the third conductive material shown in FIG. 25.

At operation 21 shown in FIG. 26, photoresist 310d is applied to third conductive metal 322c using a spin coating operation. For example, positive photoresist is spun onto backside 302b. An exemplary positive photoresist is commercially available as SPR3010 resist from Rohm and Hass.

A short soft bake is used to harden the photoresist 310d and drive out volatile components from the photoresist. Soft baking can occur at a temperature of about 95 degrees Celsius for about 60 seconds.

Figure 27:
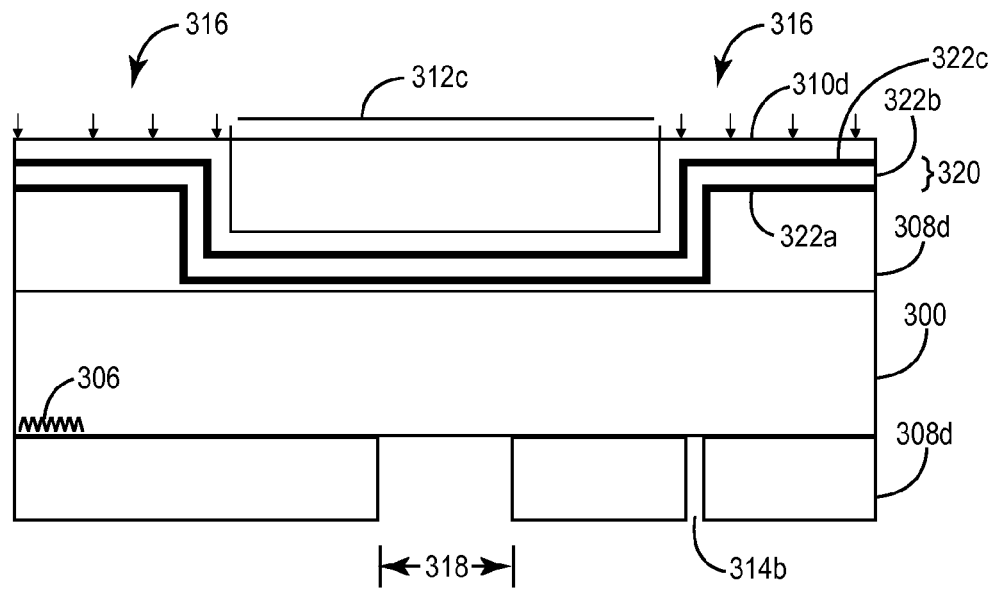
FIG. 27 depicts a mask placed over a portion of the photoresist shown in FIG. 26.

At operation 22 shown in FIG. 27, a mask 312c partially covers photoresist 310d. Photoresist 310d is then exposed to UV light 316, thereby making the photoresist soluble to the developer solution. The UV light 316 contacts photoresist 310d through an aperture at a particular wavelength for that photoresist 310d.

Figure 28:
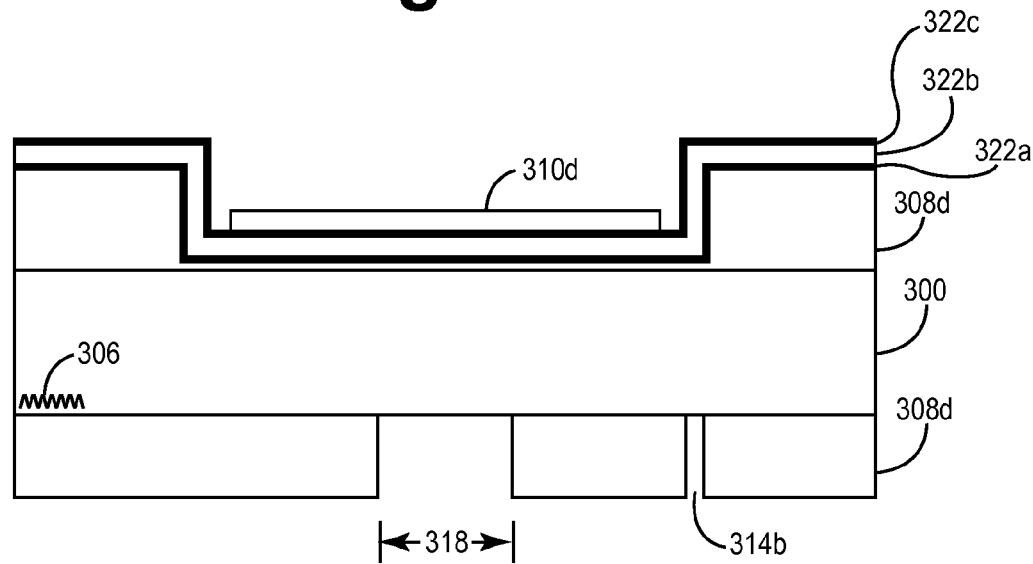
FIG. 28 depicts exposed photoresist removed from the third conductive metal shown in FIG. 27.

At operation 23 shown in FIG. 28, the photoresist 310d that was exposed to the UV light 316 is then removed through the use of an aqueous developer. As previously described, the developer solution washes over the photoresist 310d, which helps loosen the exposed photoresist 310d from the third conductive metal 322c.

Figure 29:
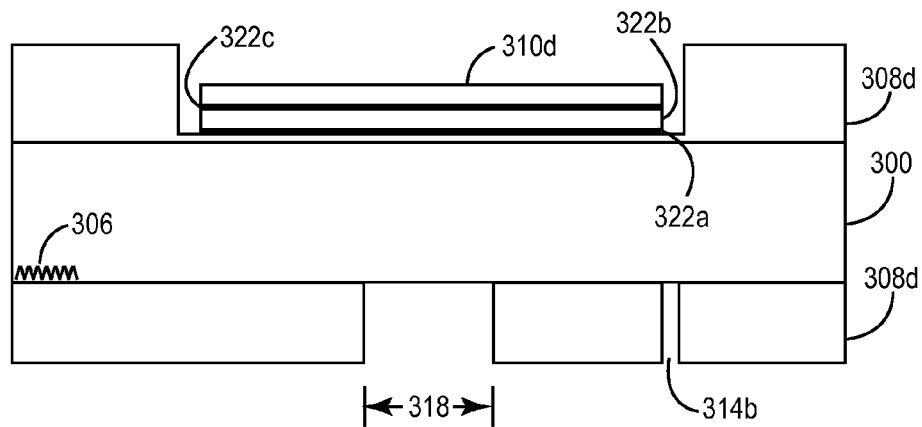
FIG. 29 depicts a portion of the first, second and third conductive materials being removed.

At operation 24 shown in FIG. 29, the first, second, and third conductive material 322a-c (e.g. Cr/Au/Ti metal) is etched. Chlorine gas is introduced into the reaction chamber of a Lam etcher and is subsequently ionized into a plasma. The plasma then etches the titanium. In contrast, a wet etching process can be used to etch the first and second conductive metals 322a,b. The wafer is placed in a TEFLON® boat, and is then placed in the wet etchant for that particular material being etched. For example, a wet etch potassium iodide (KI) and/or iodine ($I_2$) is used on the second conductive material 322b. In particular, the wafer is placed into a container of the KI/I2. After the second conductive material 322b is sufficiently etched, the wafer is then rinsed in deionized water. The wafer is then moved to the next etching operation. For example, the wafer is then moved to etchant. A standard Cr etchant is used. For example, a chrome etch can comprise a mixture of ceric ammonium nitrate and nitric acid. An exemplary chrome etch is commercially available from Fujifilm Electronic Materials, North Kingstown, R.I.

Figure 30:
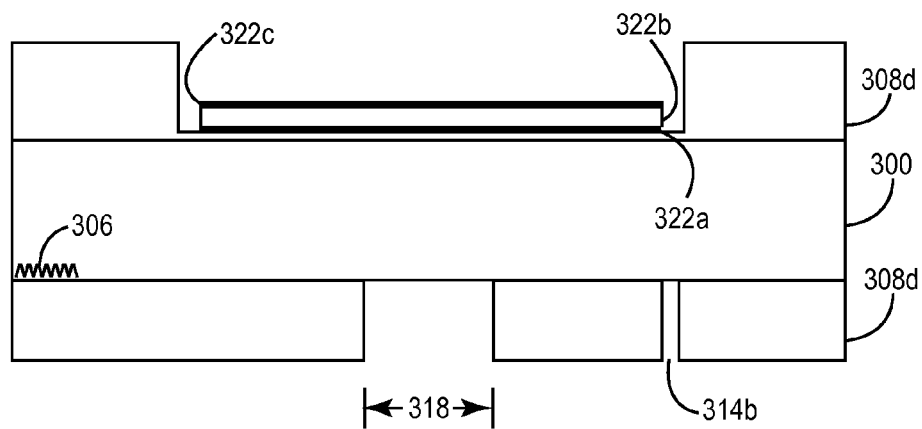
FIG. 30 depicts the remaining portion of the photoresist being removed.

At operation 25 shown in FIG. 30, the photoresist 310d is removed through, for example, an oxygen plasma RIE stripping operation.

Figure 31:
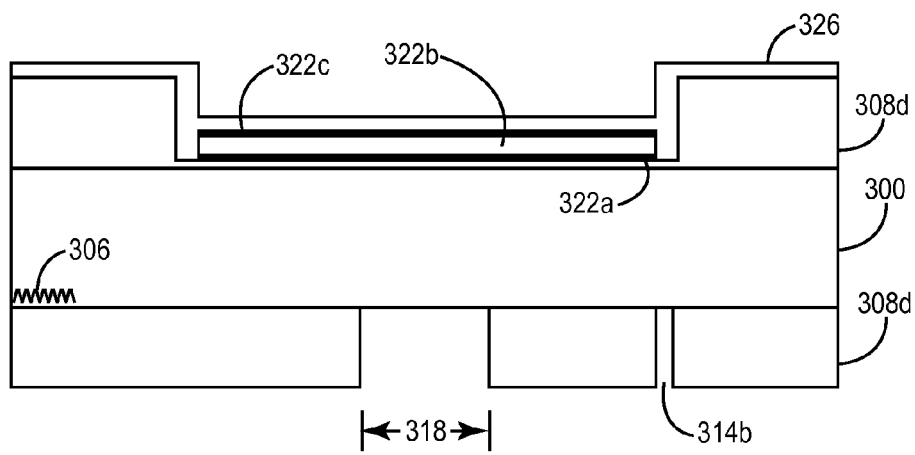
FIG. 31 depicts an insulative layer over the first, second and third conductive materials.

At operation 26 shown in FIG. 31, chemical vapor deposition (CVD) is used to deposit insulating material 326 (e.g. oxide, nitride etc.) over the thermal oxide 308d and photoresist 310d in order to create a barrier between, for example, second conductive material 322b and a conductive material 340 (e.g. gold tin) subsequently used in forming the wafer to wafer bond. Insulating material 326 is located everywhere except in the via subsequently created in operation 30.

Figure 32:
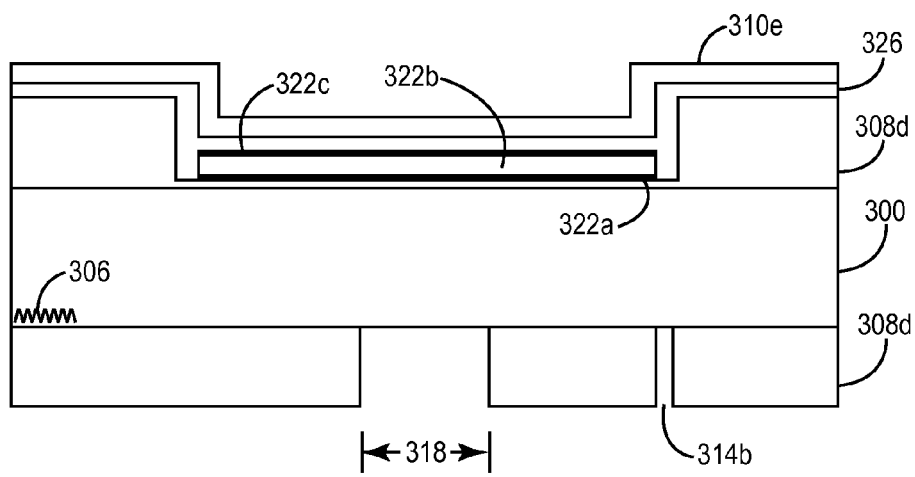
FIG. 32 depicts photoresist formed the insulative layer shown in FIG. 31.
Figure 33:
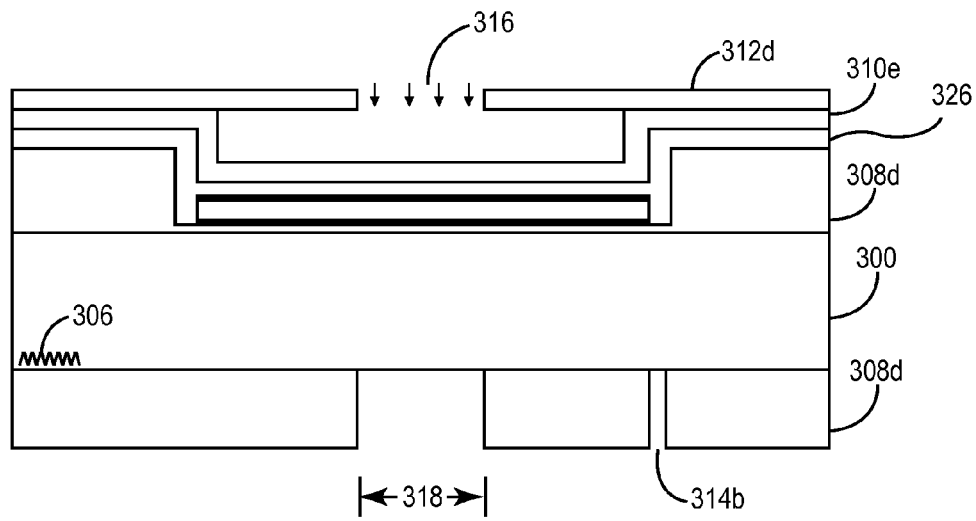
FIG. 33 depicts a mask over the photoresist as shown in FIG. 32.
Figure 34:
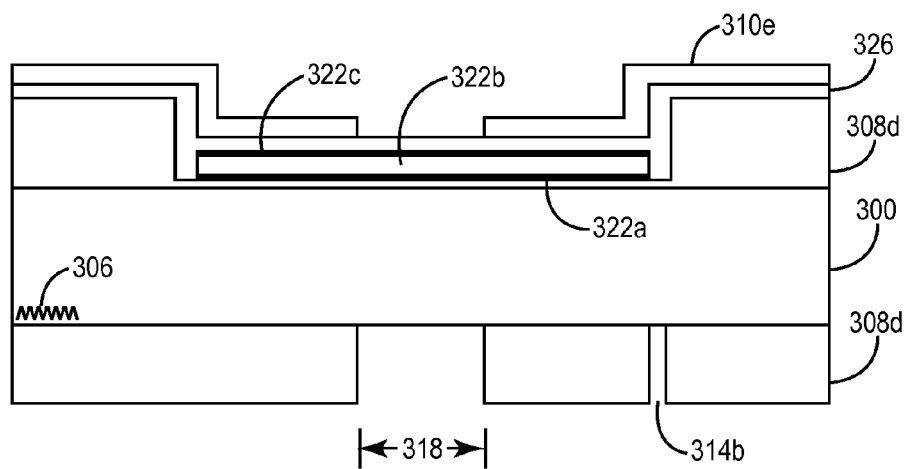
FIG. 34 depicts a portion of the photoresist removed from the substrate shown in FIG. 33.
Figure 35:
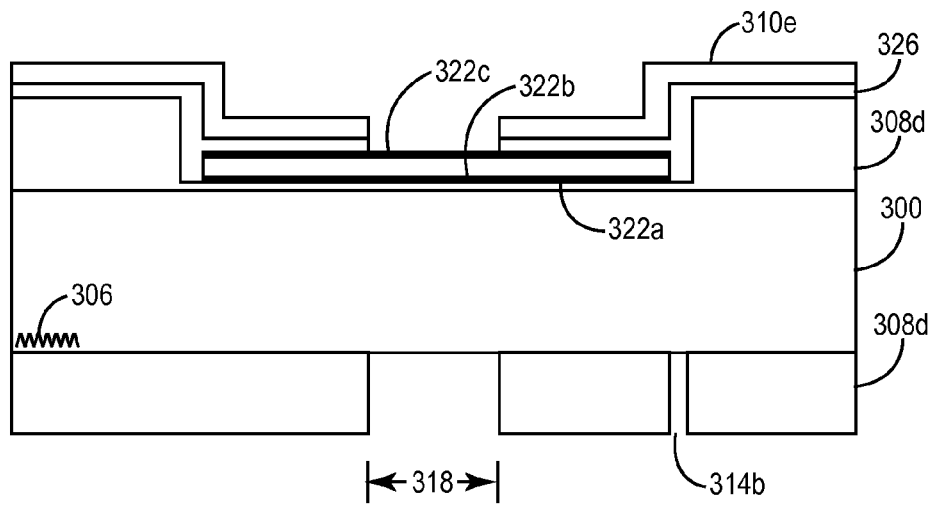
FIG. 35 a portion of the insulative layer is etched from the third conductive material as shown in FIG. 34.
Figure 36:
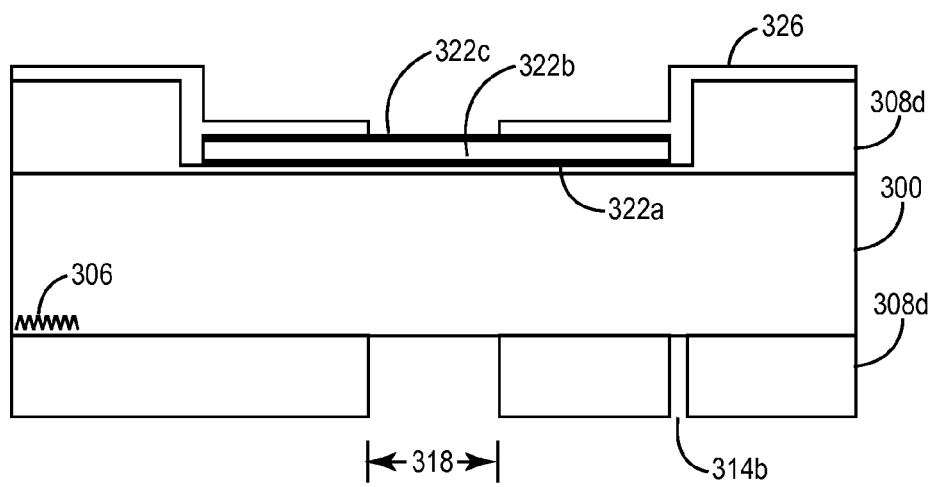
FIG. 36 depicts the removal of the remaining photoresist from the insulative layer.
Figure 37:
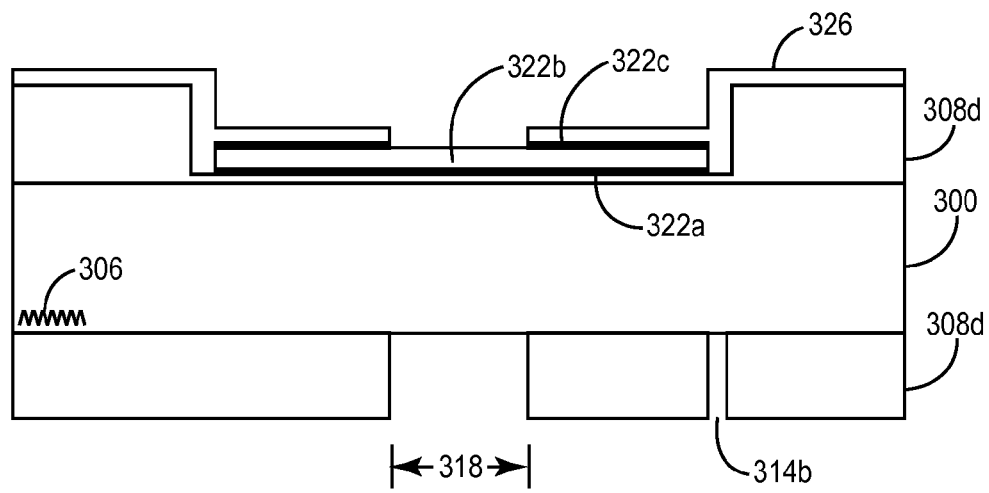
FIG. 37 depicts a portion of the third conductive material removed from the second conductive material.

At operation 27 shown in FIG. 32, photoresist 310e is applied to insulating material 326 (also referred to as barrier material). For example, a positive photoresist 310e is spun onto topside 302b using a spin coater. An exemplary positive photoresist is commercially available as SPR3010 photoresist from Rohm and Hass located in Philadelphia, Pa. A short soft bake is used to harden the photoresist 310e and drive out volatile components. At operation 28 shown in FIG. 33, a mask 312d is placed over photoresist 310e, which allows a portion of the photoresist 310e to be exposed to UV light 316 through the mask 312d. Exposed photoresist 310e is then soluble in the developer solution. At operation 29 shown in FIG. 34, exposed photoresist 310e is removed through placing aqueous based developer over the exposed photoresist 310e. At operation 30 shown in FIG. 35, insulating material 326 (e.g. oxide, nitride etc.) is etched away from the exposed area using plasma reactive ion that includes $CF_4$. At operation 31 shown in FIG. 36, the exposed photoresist 310e is removed using oxygen plasma RIE strip. At operation 32 shown in FIG. 37, a portion of third conductive material 322c, such as titanium, is removed from second conductive material 322b through a plasma etching process in which the plasma includes chlorine.

Figure 38:
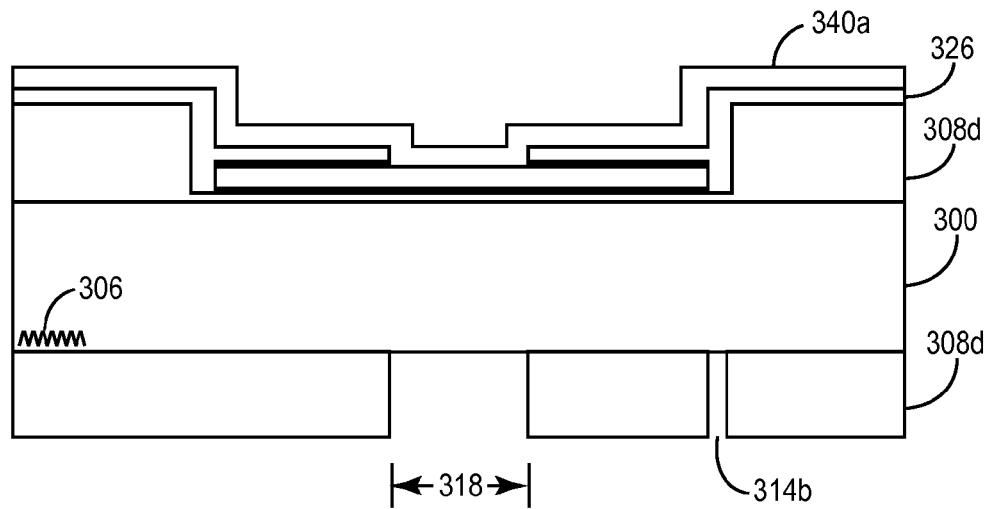
FIG. 38 depicts gold tin deposited over the second conductive material and the insulative layer.
Figure 39:
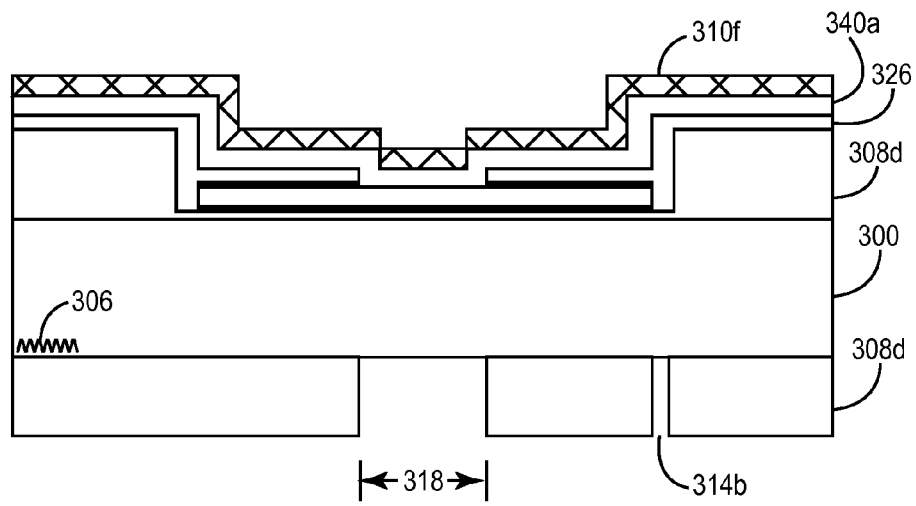
FIG. 39 depicts photoresist formed over the gold tin shown in FIG. 38.
Figure 40:
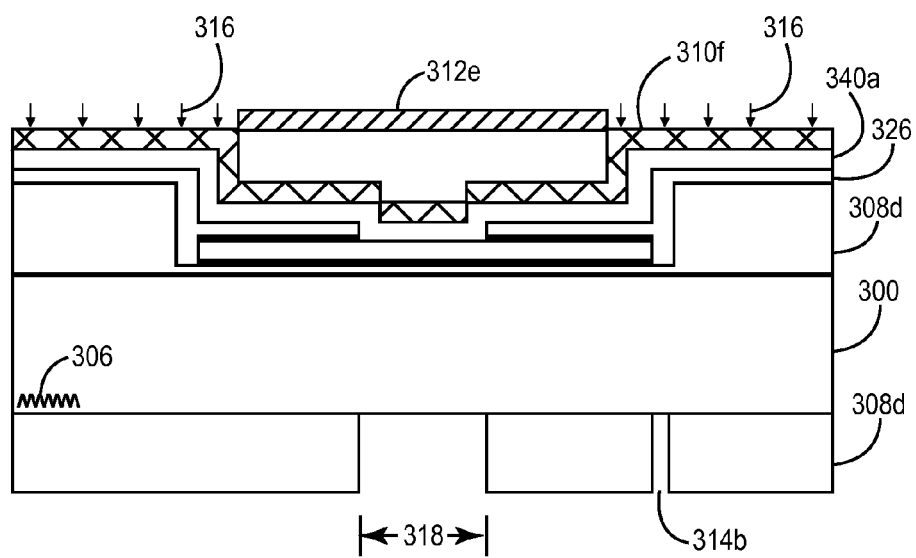
FIG. 40 depicts a mask over the photoresist shown in FIG. 39.
Figure 41:
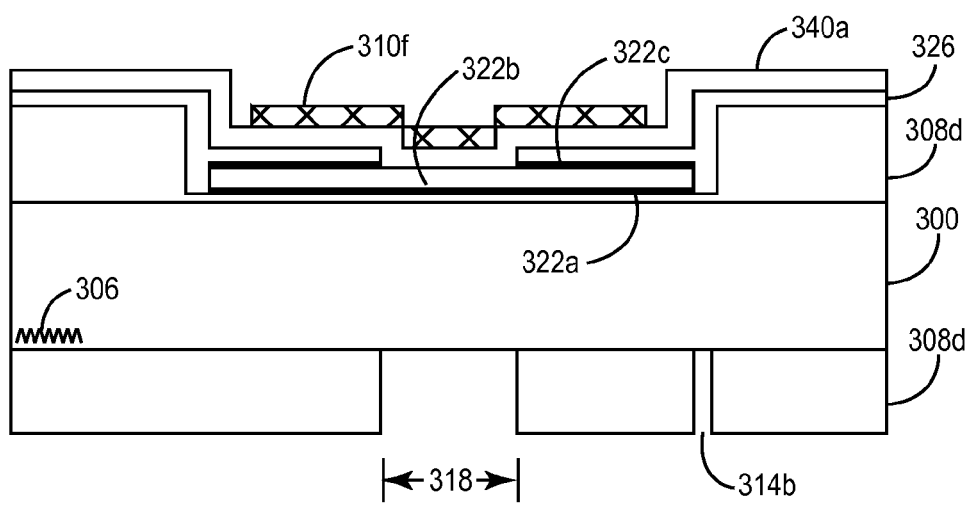
FIG. 41 depicts exposed photoresist being removed shown in FIG. 40.

At operation 33 shown in FIG. 38, a conductive material 340a such as an alloy of gold tin (AuSn) (80%/20% by weight) is deposited at a typical thickness of 1 micron over the top surface of the insulating material 326 and a portion of the second conductive material 322b (e.g. gold). Specifically, AuSn can be sputter deposited or electroplated at a thickness of about 5000 Å. In one or more other embodiments, a different thickness of AuSn can be used. In one or more embodiments, another alloy might be used such as AuSn 78%/22% can be used.

The relationship between the pad opening, AuSn diameter and AuSn thickness, and thermal oxide (or referred to as glass) thickness can be expressed as follows $$V_{total} = \pi r_{pad}^2 2 H_{glass} B$$

$$V_{1/2} = \pi r_{pad}^2 H_{glass} B = \pi r_{metal}^2 H_{metal}$$

$$\frac{r_{pad}}{r_{metal}} = \sqrt{\frac{H_{metal}}{B H_{Pad}}}$$

$V_{total}$: total solder volume
$V_{1/2}$: solder volume on each pad
$r_{pad}$: radius of pad opening
$r_{metal}$: radius of AuSn deposit
$H_{metal}$: thickness of AuSn deposit
$H_{glass}$: thickness of top glass
B: bulge factor While the equations listed above can obtain a desirable AuSn volume, pad sizes and interconnect gap, other equations could also be written to express these relationships.

Operations 34-38 shown in FIGS. 39-43 relate to a lithographic process. At operation 34 shown in FIG. 39, photoresist 310f is applied over conductive material 340a. For example, a positive photoresist 310f is spun onto conductive material 340a. A short soft bake is used to harden the photoresist 310f and drive out volatile components. At operation 35 shown in FIG. 40, a mask 312e is placed over the photoresist 310f, which allows a portion of the photoresist 310f to be exposed to UV light through the mask 312e. Exposed photoresist 310f is then soluble in the developer solution. At operation 36 shown in FIG. 41, exposed photoresist 310f is removed through placing aqueous based developer over the exposed photoresist 310f.

Figure 42:
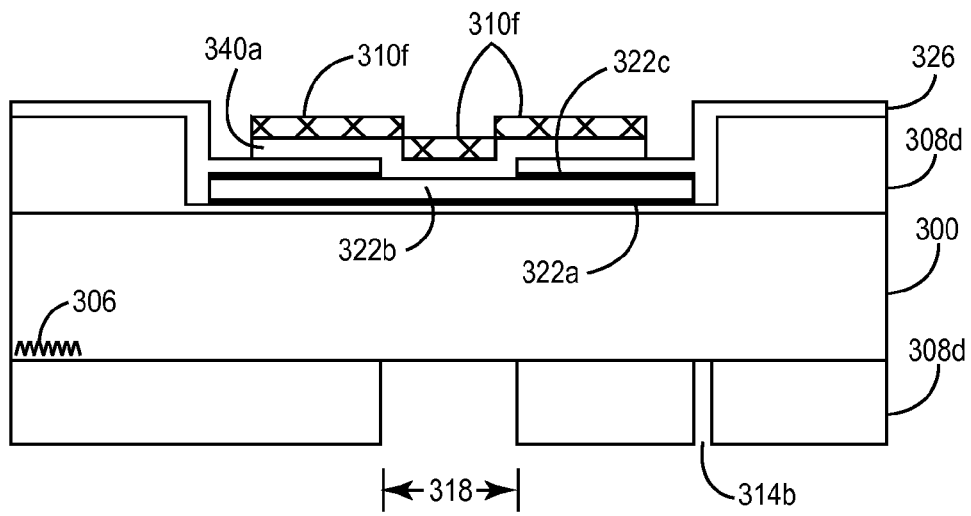
FIG. 42 depicts a portion of the gold tin being etched from the thermal oxide layer shown in FIG. 41.

At operation 37 shown in FIG. 42, exposed conductive material 340a is etched away. An exemplary plasma etch tool is the Lam 9400 TCP etcher commercially available from Lam Research located in Freemont Calif. As previously explained, exposed conductive material 340a is that material which is not covered by a mask such as the conductive material 340a located between insulating material 326, the sidewalls 327a and a bottom 327b of via 318. Conductive material 340a can comprise or consist of AuSn alloy. In one embodiment, the AuSn is about 80 weight percent of gold and 20 weight percent of tin. Sn can be etched away from Au and/or insulating material 326 using a halogen plasma etch. Exemplary halogen plasma etch includes hydrogen bromide (HBr) and/or chlorine ($Cl_2$). After a first portion of the Sn is removed from the AuSn, a first portion of Au can be etched away using a wet etch comprising of at least one of potassium iodide (KI) and/or iodine ($I_2$). After a first portion of the Au is removed, newly exposed or residual Sn can remain. Newly exposed Sn (or second portion of Sn) can be etched away through application of halogen plasma. After the second portion of the Sn is removed, newly exposed or residual Au (second portion of Au) can be removed through a wet etch. The process of alternately etching the Sn and then etching the Au is continued until the AuSn is substantially or completely removed. By using a halogen plasma to remove the Sn, a wet etch process for removing Au can proceed to completion. Specifically, all discernible Au can be removed from insulating material 326.

Figure 43:
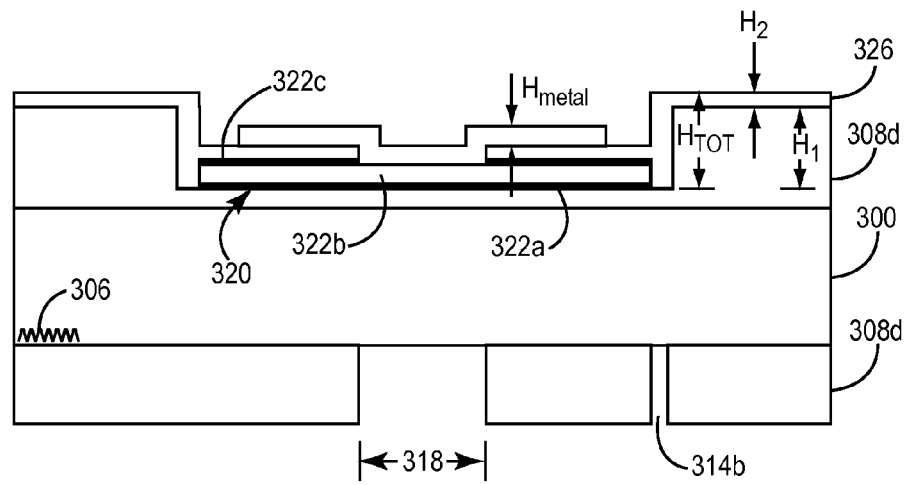
FIG. 43 depicts a portion of the photoresist being removed from the thermal oxide layer shown in FIG. 42.

At operation 38 shown in FIG. 43, the exposed photoresist 310f is removed using oxygen plasma RIE strip followed by a conventional solvent resist stripping operation.

Figure 44:
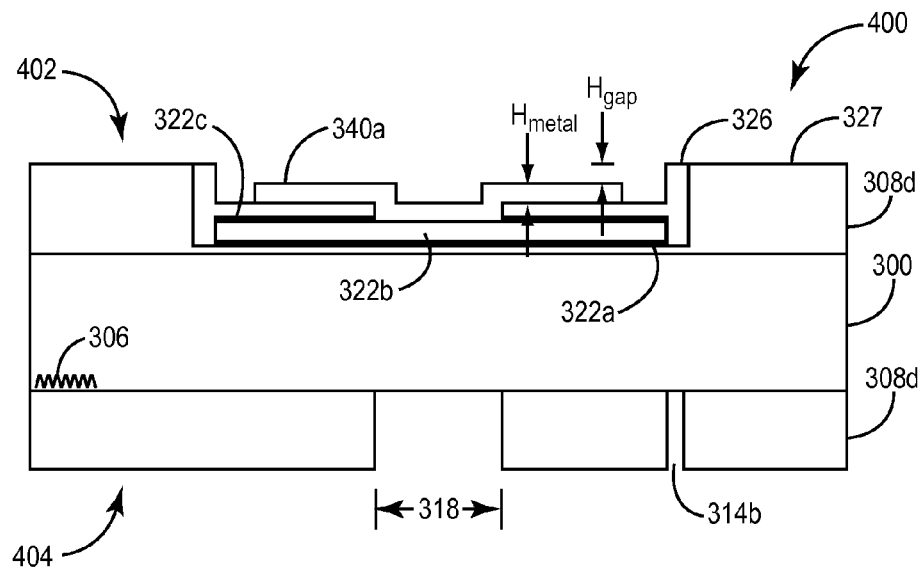
FIG. 44 depicts a top surface of the insulative layer being polished until the thermal oxide layer is exposed.
Figure 44A:
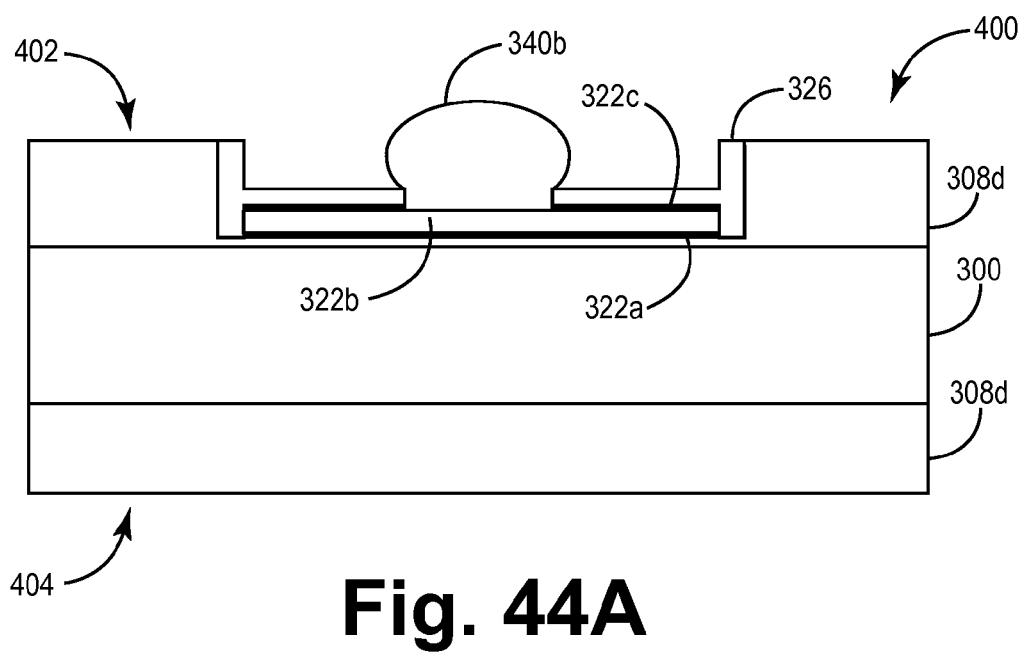
FIG. 44a depicts a finished wafer in which conductive material has undergone a reflow process.

At operation 39 shown in FIG. 44, chemical mechanical polishing (CMP) is used to polish the top surface of insulative material 326, which is removed from a top surface of barrier material 308d. After CMP is completed, a finished wafer 400 is formed. Finished wafer 400 has a frontside 402 (top side) and a bottom side 404. FIGS. 44-44a show details of one or more embodiments of a wafer before conductive material 340a has undergone a reflow process to form a conductive pad 340c. Skilled artisans appreciate that it is unnecessary to polish until the thermal oxide is exposed.

The height ($H_{340a}$) of the conductive material 340a ranges from about 0.25 mircon to about 0.75 mircon. Preferably, the $H_{340a}$ has a height of 0.5 micron, which is much smaller than the height of the via $H_{via}$, which is 1.5 mircon. Referring to FIG. 44a, the height of H1 is 1.5 micron whereas the height of H2 is 0.2 micron. Total height $H_{total}$ is H1+H2, which equals 1.7 microns. $H_{gap}$ is the height between $H_{340a}$ (also referred to as $H_{metal}$) and the top surface 327 of barrier material 308d. As shown in FIG. 44A, conductive pad 340c, after the reflow process, becomes substantially spherical and is vertically higher than $H_{340a}$. Preferably, $H_{pad}$ ranges from about 1.5 microns to about 2 microns. Preferably, the $H_{pad}$ has a height of 1.75 microns.

Figure 45:
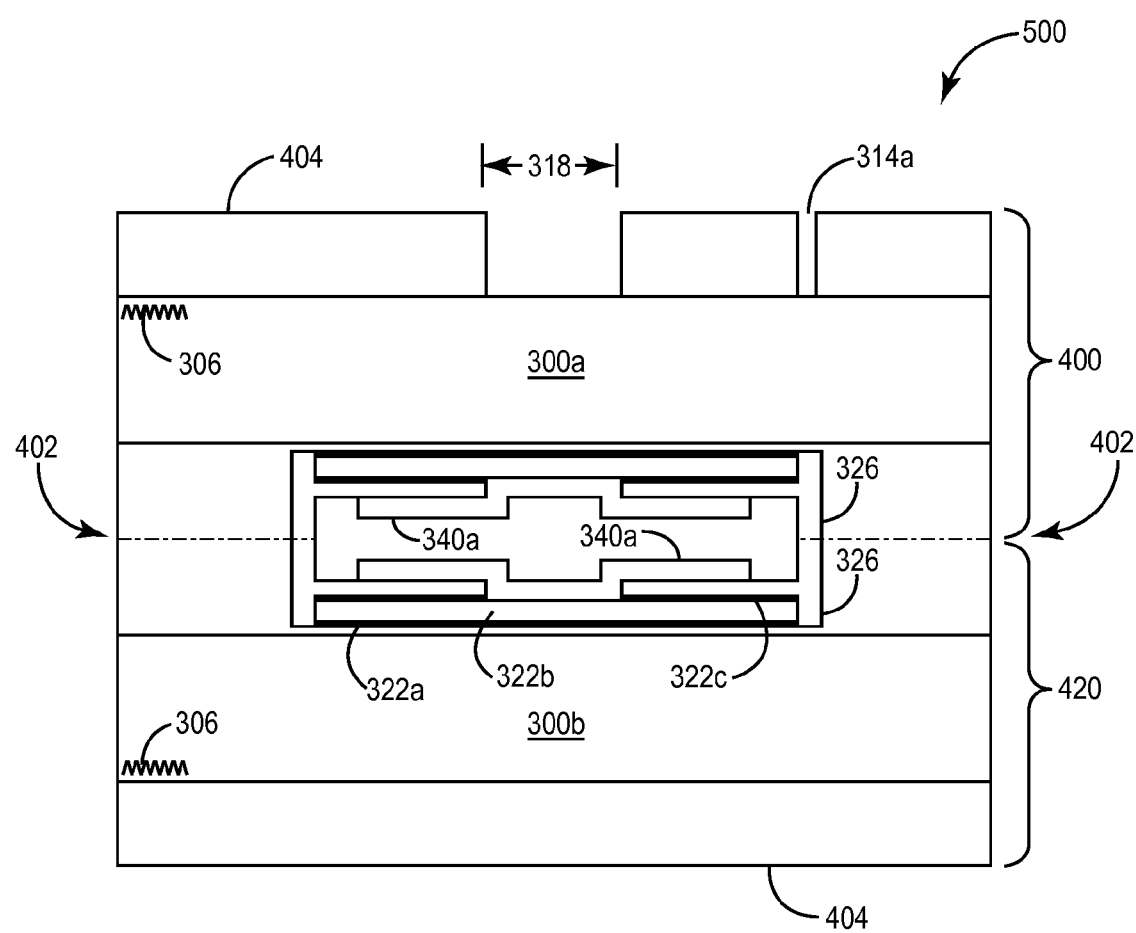
FIG. 45 depicts a frontside of a first substrate coupled to a frontside of a second substrate.
Figure 46:
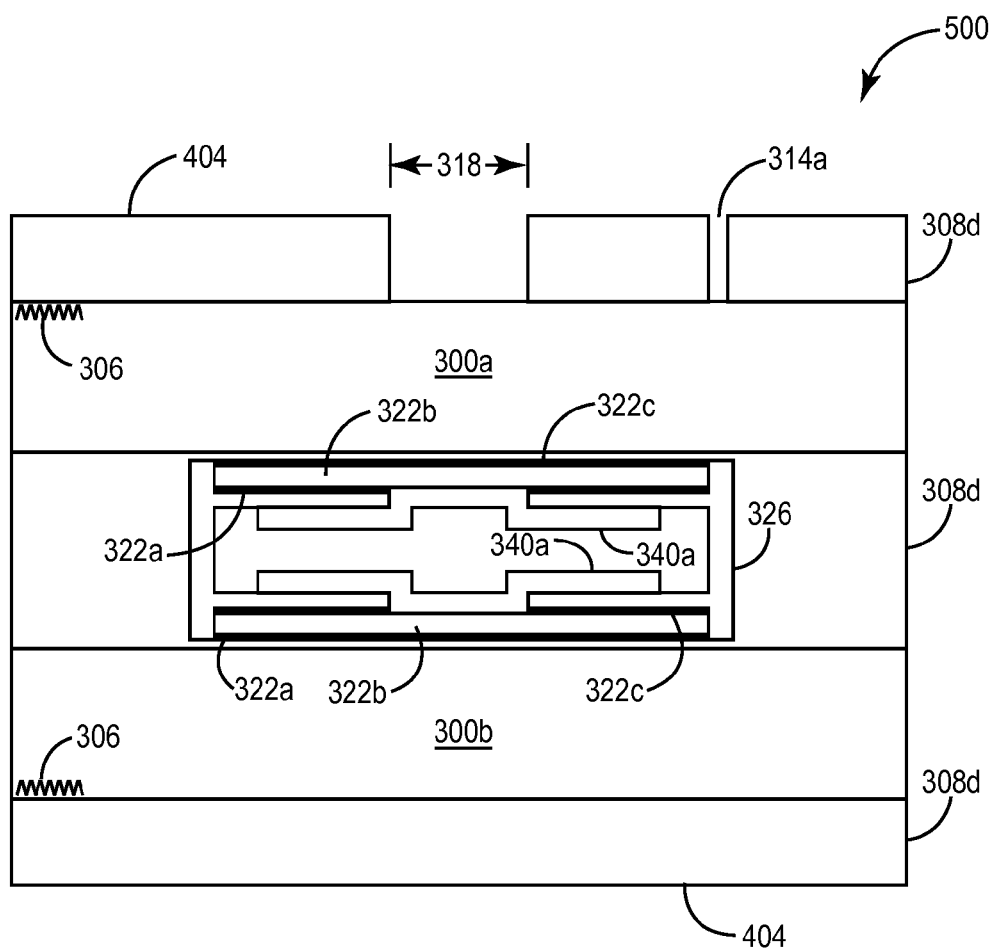
FIG. 46 depicts a hermetic bond between the first and second substrates.

At operation 40 shown in FIG. 45, a wafer to wafer bond (also referred to as a substrate 300a to substrate 300b bond) is formed in the wafer bonding chamber of a EVG 500 Series equipment commercially available from EV Group located in Tempe, Ariz.). The wafer bonding chamber has a temperature at about 200 degrees Celsius and operates at atmospheric pressure to form the wafer to wafer bond.

The finished wafer 400 can be joined or bonded to another finished wafer 420, as shown by the wafer-to-wafer bond 500. In one embodiment, wafer 420 is a mirror image of wafer 402.

The face side 402 of finished wafer 400 is aligned and bonded to the face side 402 of finished wafer 420. Finished wafer 420 can be the same or different as finished wafer 400. For example, finished wafer 420 is different from finished wafer 400 in that finished wafer 402 lacks vias 314b and 318. The first substrate 400 bonded to the second substrate 420 can be a glass to glass bond, glass-silicon bond, or silicon-silicon bond. The glass to glass bond, glass-silicon bond, or silicon-silicon bond can be formed across an entire wafer with the exception of small recessed areas containing the pad structures At operation 41 shown in FIG. 46, bonding occurs. Completion of the bond between finished wafer 400 and finished wafer 402 occurs at a temperature that is generally less than 250° C.

Figure 47:
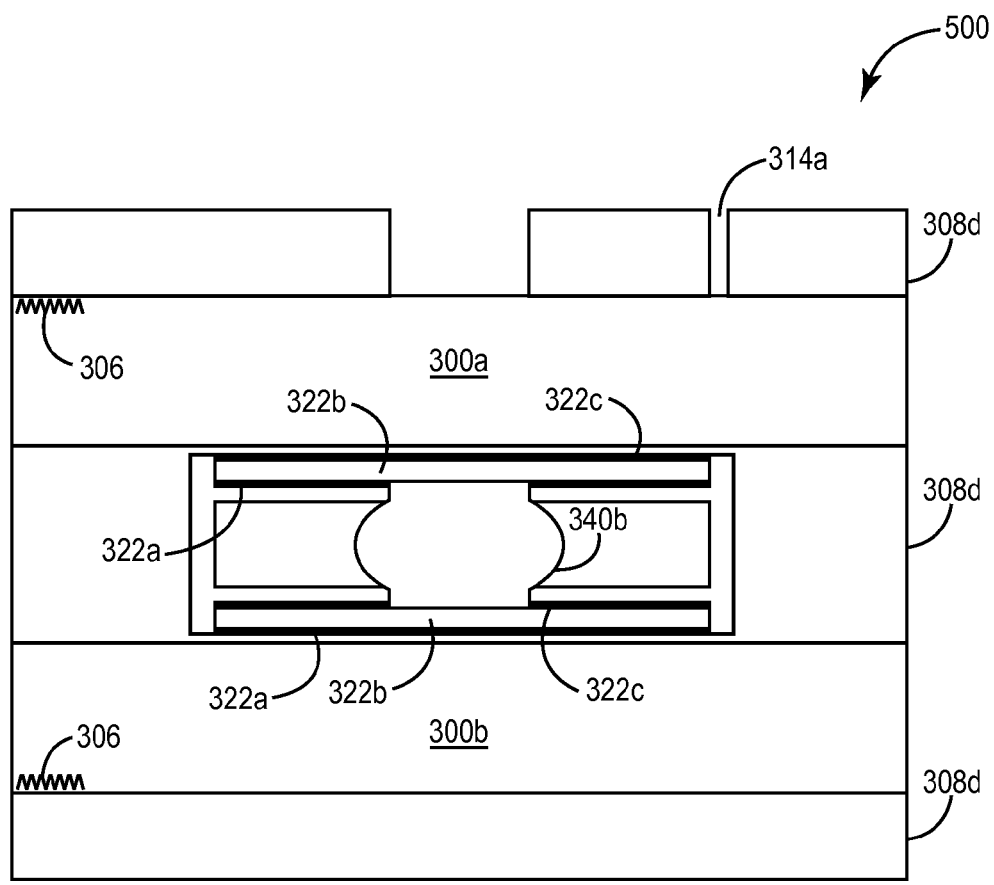
FIG. 47 depicts the gold tin extending between the first and second substrates to form an electrical connection.

At operation 42 shown in FIG. 47, the conductive material 340a (e.g. AuSn) undergoes a reflow process in a chamber of vacuum pressure furnace such as SST model 3130 is commercially available from SST International located in Downey, Calif. The conductive material 340a can generally be ref lowed at a temperature of about 305° C. and a N2 ambient.

Figure 48:
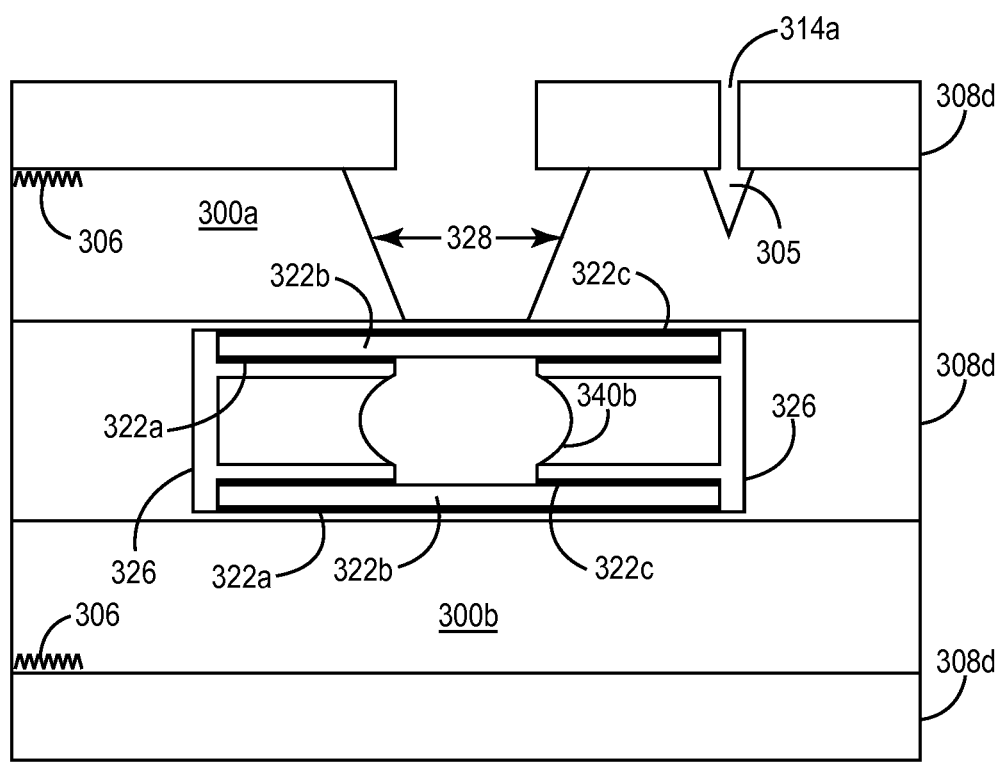
FIG. 48 depicts vias formed through a substrate.
Figure 49:
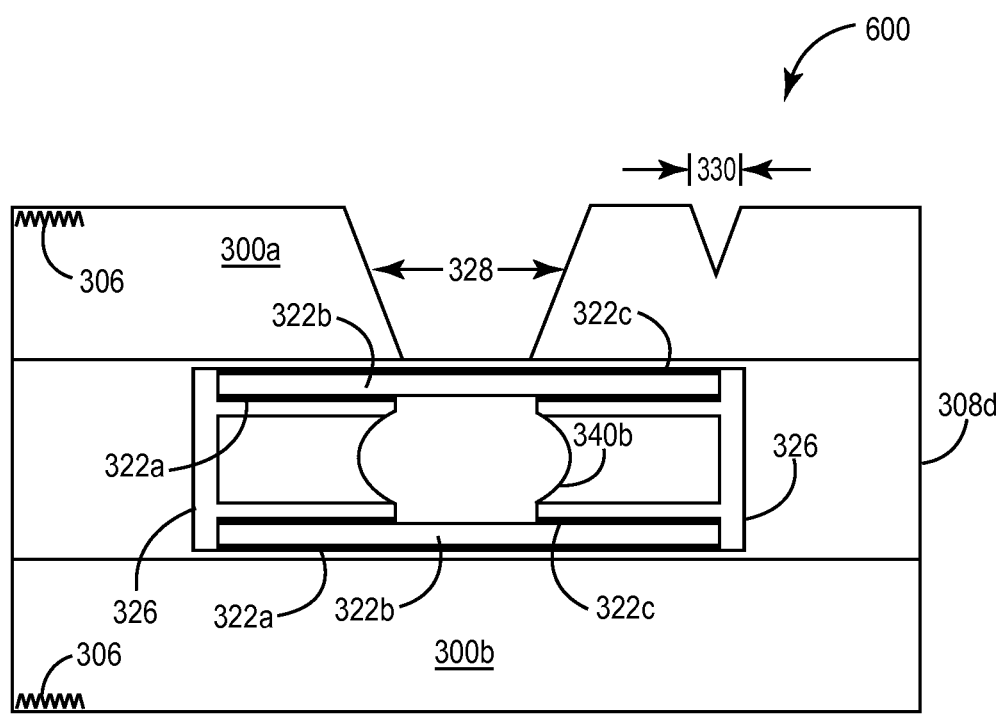
FIG. 49 depicts thermal oxide being removed from one of the substrates shown in FIG. 48.

At operation 43 shown in FIG. 48, via 328, 330 are formed in substrate 300 through an etching process. For example, a wet etch can be used that comprises tetramethylammonium hydroxide (TMAH). The via 328, 330 is formed in a substantially triangular shape by the TMAH preferentially etching along a crystal lattice of the silicon. By etching along a crystal lattice of the silicon, a sloped via 328, 330 is achieved. At operation 44 shown in FIG. 49, the barrier material 308d is stripped from substrate 300.

Table 1 presented below provides a brief description of the process operations used to form a wafer to wafer bond as described in the text accompanying each figure.

TABLE 1

Brief summary of each operation

| Operation number | Figure | OPERATION |
|---|---|---|
| 1 | 6 | Grind backside of substrate |
| 2 | 7 | Clean substrate |
| 3 | 8 | Form barrier over the substrate |
| 4 | 9 | Scribe backside of the substrate |
| 5 | 10 | Remove barrier from the substrate |
| 6 | 11 | Clean substrate |
| 7 | 12 | Form thermal oxide over the substrate |
| 8 | 13 | Deposit photoresist over the thermal oxide |
| 9 | 14 | Place mask over the photoresist |
| 10 | 15 | Remove exposed photoresist |
| 11 | 16 | Dry etch thermal oxide |
| 12 | 17 | Remove remaining photoresist |
| 13 | 18 | Clean substrate |
| 14 | 19 | Form thermal oxide over the substrate |
| 15 | 20 | Apply photoresist to backside of the substrate |
| 16 | 21 | Place mask over the photoresist |
| 17 | 22 | Remove exposed photoresist |
| 18 | 23 | Dry etch backside of substrate to form vias |
| 19 | 24 | Remove resist |
| 20 | 25 | Form adhesion or barrier material over thermal oxide |
| 21 | 26 | Deposit photoresist over the barrier material |
| 22 | 27 | Place mask over photoresist |
| 23 | 28 | Remove exposed photoresist |
| 24 | 29 | Etch barrier material |
| 25 | 30 | Remove photoresist from barrier material |
| 26 | 31 | Deposit oxide over the barrier material |
| 27 | 32 | Deposit photoresist over the oxide material |
| 28 | 33 | Place mask over the photoresist |
| 29 | 34 | Remove exposed photoresist |
| 30 | 35 | Etch oxide |

TABLE 1-continued

Brief summary of each operation

| Operation number | Figure | OPERATION |
|---|---|---|
| 31 | 36 | Remove photoresist |
| 32 | 37 | Remove titanium |
| 33 | 38 | Deposit conductive material to form a conductive pad |
| 34 | 39 | Apply photoresist to conductive material |
| 35 | 40 | Expose photoresist through mask |
| 36 | 41 | Remove exposed photoresist |
| 37 | 42 | Etch conductive material |
| 38 | 43 | Remove photoresist from conductive pad |
| 39 | 44 | Polish top surface |
| 40 | 45 | Couple the first and second substrates |
| 41 | 46 | Stabilize the bond |
| 42 | 47 | Reflow the conductive material in the conductive pad |
| 43 | 48 | Etch vias into the substrate |
| 44 | 49 | Remove thermal oxide |

Figure 50:
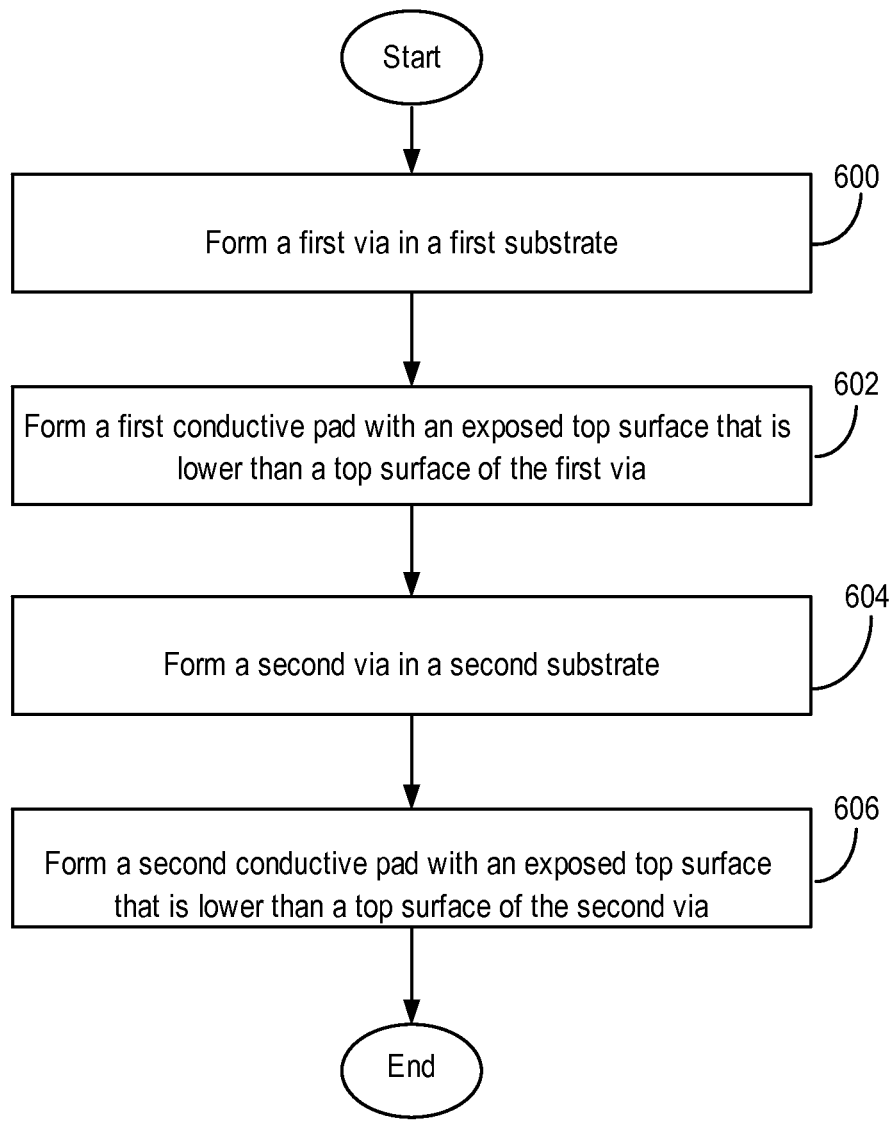
FIG. 50 depicts a flow diagram of a method for forming wafer to wafer bond.

FIG. 50 is a flow diagram for forming a wafer to wafer bond. At block 600, a first via is formed in a first side of a first substrate. At block 602, a first conductive pad is formed in the first via such that an exposed top surface of the first conductive pad is lower than a top surface of the first via. At block 604, a second via is formed in a first side of a second substrate. At block 606, a second conductive pad is formed in the second via such that an exposed top surface of the second conductive pad is lower than a top surface of the second via.

The process disclosed herein significantly simplifies the polishing process. For example, the polishing process, discussed relative to the CMP description of operation 39, subjects only one material—oxide or nitride to polishing. In contrast, the conventional approach can have oxide and metal exposed to the CMP process. Additionally, the process also allows for electrical connections wherever electrical connections are needed and there is no need to add "dummy" connections. For example, in one conventional process, conductive pads are on the same plane as the oxide. Therefore, more than one substance (e.g. conductive pad and oxide etc.) is exposed to CMP at the same time. To ensure CMP polish is evenly applied across the surface, the conventional process requires numerous conductive pads to be evenly distributed over the wafer surface. In essence, the extra conductive pads serve as a loading effect to facilitate the CMP but do not contribute to the electrical connections. In one or more other embodiments, the solderable pad could be gold over titanium or gold over chromium. The underlying titanium or chromium layer(s) need only be thick enough to provide good adhesion. For example, titanium or chromium layer(s) should be in the 100s of Angstroms. Preferably, the range of titanium should be about 100 Angstroms to about 400 Angstroms. Preferably, the range of chromium is about 200 Angstroms to about 400 Angstroms. Titanium would still be employed over the gold in areas covered with glass to improve the adhesion of the glass to the pad.

In yet another embodiment related to the solderable pad, gold could be replaced with platinum. The platinum pad is not consumed by the solder; therefore, the liquidus does not change due to the absorption of the gold. Preferably, the platinum thickness can range from about 100 to about 1000 Å thick. More preferably, the platinum thickness can range from about 100 to about 5000 Å thick. Using platinum in place of gold can be done for both the pad under the AuSn solder as well as a pad to which the AuSn might be joined during solder reflow.

Conductive pads or bumps can join in the middle of a via. In another embodiment, conductive pads or bumps can be located on one wafer making connection to pads on the mating wafer.

In one or more other embodiments, other metals such as palladium, copper, nickel, rhodium, tin, could be used in place of the gold in the solderable pads.

Figure 51:
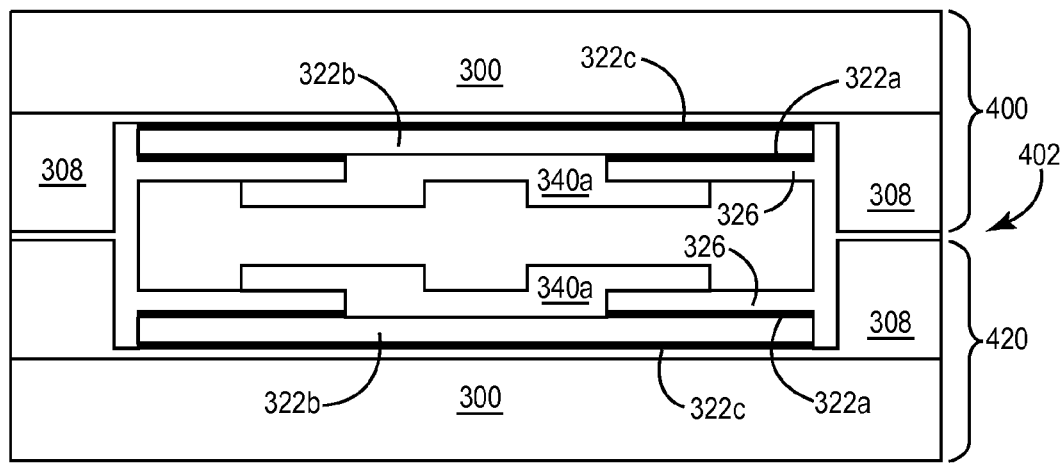
FIG. 51 a schematic side view of a wafer to wafer bond with an oxide overlap.
Figure 52:
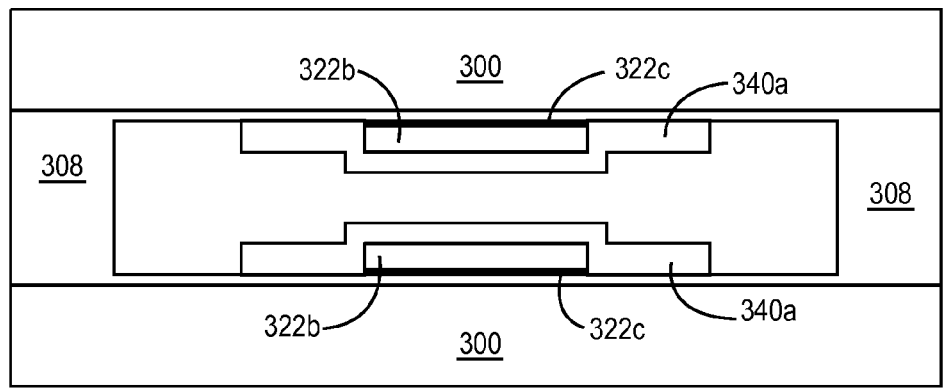
FIG. 52 a schematic side view of a wafer to wafer bond without an oxide overlap.

In one or more embodiments related to solderable pads (the Ti/Au/Ti or equivalent), rather than having the glass overlap the metal and define the conductive pad's 320 perimeter as shown in FIG. 51, the glass can be pulled back and the pad 320 size and shape is defined by the patterning of the pad 320 itself as shown in FIG. 52. The embodiment of FIG. 52 includes a pad 320, defined by pattern and etch processes, that tends to wick less under the glass as it consumes the gold.

Although various embodiments of the invention have been described and illustrated with reference to specific embodiments thereof, it is not intended that the invention be limited to such illustrative embodiments. For example, it is to be appreciated that while specific examples of the processing equipment are provided, a variety of types of processing equipment can be used. Additionally, skilled artisans appreciate that while a positive photoresist was used in the process described herein, a negative photoresist could be used in place of the positive photoresist. If a negative photoresist is used, the mask should be configured to accommodate the negative photoresist.

Additionally, alternate processes and flows could be used to achieve the same end result. For example, a lift-off process rather than deposit, pattern and etch can be used to form the structures shown in FIG. 25 and FIG. 38-43. An exemplary lift off process may be seen with respect to U.S. Pat. No. 4,564,584, entitled PHOTORESIST LIFT-OFF PROCESS FOR FABRICATING SEMICONDUCTOR DEVICES, issued to Fredericks et al on Jan. 14, 1986, the disclosure of which is incorporated by reference in its entirety herein.

Combining low temperature hermetic wafer bonding with an electrical interconnection is easier and cheaper to implement than conventional methods. For example, since each conductive pad is placed in a recessed cavity, the conductive pad does not interfere with CMP. Moreover, electrical connections can be provided in any location on the wafer since a solder bump is not placed on the surface of the wafer. Moreover, there is no need to add "dummy" connections merely to provide a uniform distribution of conductive pads across the wafer.

Figure 53:
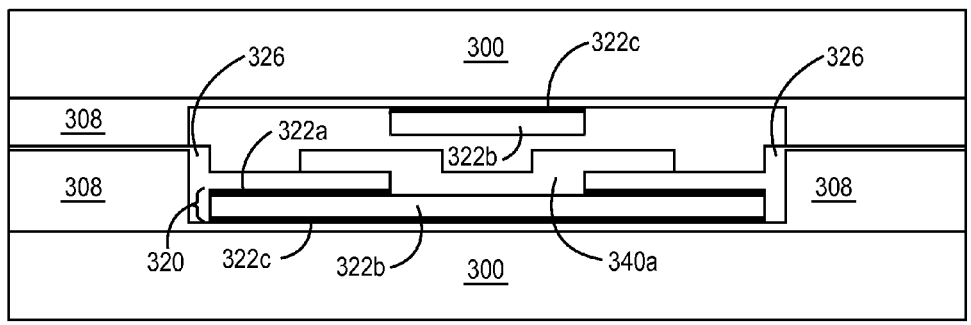
FIG. 53 is a schematic view of a bump to pad structure before a reflow process.
Figure 54:
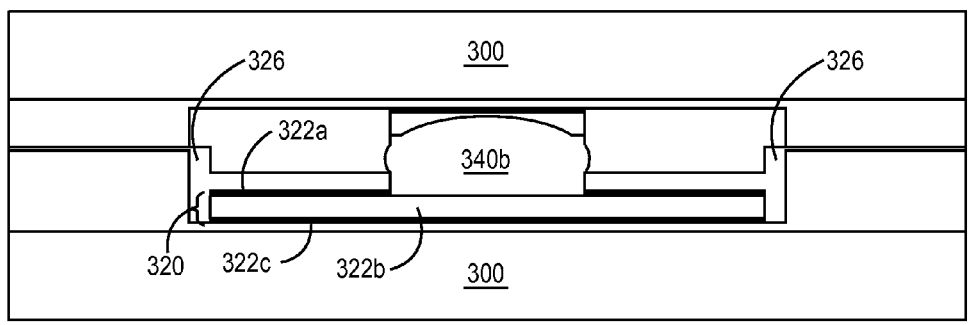
FIG. 54 is a schematic view of the bump to pad structure shown in FIG. 53 after a reflow process.

The present disclosure presents various embodiments for creating electrical interconnections between wafers using AuSn or other alloy deposited or otherwise applied to both opposing pads 320 to be connected. The present disclosure can also be applied to a bump-to-pad configuration, as shown in FIG. 53-54. Rather than two bumps coalescing as previously described, a single bump undergoes a reflow process and then makes contact with a solderable pad slightly below the surface of the mating wafer, as is shown in FIG. 54. It is also possible to apply the AuSn or other connection-forming alloy to just one of the surfaces, the other side being a pad 320, formed of to which the AuSn wets as it forms its near spherical shape during melting.

The bump-to-pad configuration can reduce cost by applying the AuSn to only one wafer rather than both. The bump-to-pad configuration also allows the pad-only wafer to be processed in a manner that might not be compatible with the wafer if the wafer had AuSn on the surface. For example oxygen plasma cleaning or oxidizing acids would oxidize the Sn in the AuSn and hinder a subsequent spherical or ball formation. This configuration however would not affect the wettability of a gold pad on a wafer.

The interconnect is accomplished the same way with the single-sided design as with the two-sided design previously disclosed. Wafers are brought together with pads aligned and the wafer stack is heated above the liquidus (280° C.) of the AuSn. The AuSn will dewet from the glass annulus around the wettable pad and attempt to form a sphere to reduce surface energy. The AuSn volume is sufficient to cause the near-spherical AuSn to touch the wettable (most likely gold) pad on the opposing wafer and form the electrical contact. Again, no liquid or paste flux is used or is desired. This can be accomplished during or after the wafer bonding heat activation process.

The 80/20 weight percent AuSn alloy was described previously and is well-suited to this application because of its ability to be deposited, patterned and reflowed without flux. As mentioned previously, oxygen should be eliminated from the atmosphere to preclude oxidation during heating. Other alloys in the AuSn system such as AuSn 78/22 could prove beneficial. The additional Sn content allows the liquid AuSn to consume dissolved gold from the wettable pads without raising the liquidus temperature. This is evident from the AuSn binary phase diagram. AuSn 79/21 and other alloys are possible.

Other suitable alloys could include binary or higher-order combinations of Au, Sn, Ag, etc. Selection of an alloy with a desired liquidus temperature and wetting properties can provide preferable results.

The interconnect method described herein can be applied to any number of wafers properly aligned in a stack. Single and double-sided bonding could even be mixed within the stack. Single and double-sided bonding can be accomplished either serially by the addition of one or more wafers at a time to a previously processed subset of wafers or by processing the entire stack simultaneously.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. Accordingly, a first conductive material comprising titanium includes a first conductive material consisting essentially of, or consisting of, a titanium.

The description of the invention presented herein is merely exemplary in nature and, thus, variations that do not depart from the gist of the invention are intended to be within the scope of the invention. Variations are not to be regarded as a departure from the spirit and scope of the invention.

The invention claimed is:

1. A method for forming an implantable medical device that includes a component comprising a first substrate bonded to a second substrate, the method comprising:
    forming a first via in a first side of a first substrate;
    introducing insulative material into the first via;
    introducing an alloy over the insulative material, the alloy consists essentially of gold tin (AuSn);
    removing a first portion of tin (Sn) from the alloy through a halogen plasma;
    exposing a first portion of gold (Au) from a remaining portion of the alloy in response to removing the first portion of the Sn; and
    removing the first portion of the Au through a wet etch.

2. The method of claim 1 further comprising:
    exposing a second portion of Sn in response to removing the first portion of Au.

3. The method of claim 2 further comprising:
removing the second portion of Sn through the halogen plasma.

4. The method of claim 3 further comprising:
exposing a second portion of Au in response to removing the second portion of Sn.

5. The method of claim 4 further comprising:
removing the second portion of Au through the wet etch.

6. The method of claim 5 wherein AuSn is removed from an insulating material.

7. The method of claim 6, wherein Au is removed from an insulating material.

8. The method of claim 1 wherein the AuSn is about 80/20 percent by weight of AuSn.

9. The method of claim 1 wherein the AuSn is about 78/22 percent by weight of AuSn.

10. A method for forming an implantable medical device that includes a component comprising a first substrate bonded to a second substrate, the method comprising:
removing a first portion of tin (Sn) from gold tin (AuSn) through a halogen plasma;
exposing a first portion of gold (Au) from a remaining portion of AuSn in response to removing the first portion of Sn;
removing the first portion of Au from the remaining portion AuSn through a wet etch; and
exposing a second portion of Sn in response to removing the first portion of Au.

11. The method of claim 10 further comprising:
removing the second portion of Sn through the halogen plasma.

12. The method of claim 11 further comprising:
exposing a second portion of Au in response to removing the second portion of Sn.

13. The method of claim 12 further comprising:
removing the second portion of Au through the wet etch.

14. The method of claim 13 wherein AuSn is removed from the insulating material.

15. The method of claim 13, wherein Au is removed from the insulating material.

16. The method of claim 10 wherein the AuSn is about 80/20 percent by weight of AuSn.

17. The method of claim 10 wherein the AuSn is about 78/22 percent by weight of AuSn.

18. A method for forming an implantable medical device that includes a component comprising a first substrate bonded to a second substrate, the method comprising:
(a) forming a first via in a first side of a first substrate;
(b) introducing insulative material into the first via;
(c) introducing an alloy over the insulative material, the alloy comprising gold tin (AuSn);
(d) removing a portion of tin (Sn) from the alloy through a halogen plasma;
(e) exposing a portion of gold (Au) from a remaining portion of the alloy in response to removing the portion of Sn;
(f) removing the portion of Au from the remaining portion through a wet etch,
wherein steps (d) through (f) are repeatedly performed until all discernible AuSn is removed from a the insulative material.

* * * * *

UNITED STATES PATENT AND TRADEMARK OFFICE
CERTIFICATE OF CORRECTION

PATENT NO. : 8,513,120 B2  
APPLICATION NO. : 13/097026  
DATED : August 20, 2013  
INVENTOR(S) : Bruce C. Fleischhauer Page 1 of 1

It is certified that error appears in the above-identified patent and that said Letters Patent is hereby corrected as shown below:

On the Title Page  
Item (57) Abstract, line 7-8, delete "The first portion of the Au through a wet etch" and insert in place thereof -- The first portion of the Au is removed through a wet etch --;

In the Claims  
Column 26, line 29, please delete "is removed from a the insulative" and insert therefor -- is removed from the insulative --.

Signed and Sealed this  
Second Day of September, 2014

Michelle K. Lee  
*Deputy Director of the United States Patent and Trademark Office*